(12) United States Patent
Koths et al.

(10) Patent No.: US 6,184,354 B1
(45) Date of Patent: Feb. 6, 2001

(54) SOLUBLE EXTRACELLULAR DOMAIN OF HUMAN M-CSF RECEPTOR

(75) Inventors: Kirston Koths, El Cerrito; Eric Taylor, Oakland, both of CA (US)

(73) Assignee: Chiron Corporation, Emeryville, CA (US)

( * ) Notice: Under 35 U.S.C. 154(b), the term of this patent shall be extended for 0 days.

(21) Appl. No.: 08/462,794

(22) Filed: Jun. 5, 1995

Related U.S. Application Data

(63) Continuation of application No. 08/351,292, filed as application No. PCT/US93/05548 on Jun. 9, 1993, now Pat. No. 5,866,114, which is a continuation-in-part of application No. 07/896,512, filed on Jun. 9, 1992, now abandoned.

(51) Int. Cl.⁷ .......................... C07K 14/53; C07K 14/52; C07K 14/435

(52) U.S. Cl. .......................... 530/351; 530/350

(58) Field of Search .................. 530/350, 351; 435/69.1; 514/2, 8

(56) References Cited

U.S. PATENT DOCUMENTS

| | | | |
|---|---|---|---|
| 4,179,337 | 12/1979 | Davis et al. | 435/181 |
| 4,582,788 | 4/1986 | Erlich | 435/6 |
| 4,672,108 | 6/1987 | Kung et al. | 530/351 |
| 4,683,195 | 7/1987 | Mullis et al. | 435/6 |
| 4,683,202 | 7/1987 | Mullis | 435/91 |
| 4,755,363 | 7/1988 | Fujita et al. | 422/245 |
| 4,833,233 | 5/1989 | Carter | 530/363 |
| 4,847,201 | 7/1989 | Kawasaki et al. | 435/70 |
| 4,881,175 | 11/1989 | Ladner | 364/496 |
| 4,908,773 | 3/1990 | Pantoliano et al. | 364/496 |
| 4,929,700 | 5/1990 | Halenbeck et al. | 530/351 |
| 4,946,778 | 8/1990 | Ladner et al. | 435/69.6 |
| 4,966,911 | 10/1990 | Clark et al. | 514/385 |
| 5,032,676 | 7/1991 | Deeley et al. | 530/351 |
| 5,589,456 | * 12/1996 | Smith et al. | 514/12 |

FOREIGN PATENT DOCUMENTS

| | | |
|---|---|---|
| 0 272 779 A2 | 6/1988 | (EP) . |
| 0 344 796 A2 | 12/1989 | (EP) . |
| 0 402 070 A1 | 12/1990 | (EP) . |
| WO 88/08003 | 10/1988 | (WO) . |
| WO 91/09943 | 7/1991 | (WO) . |
| WO 92/21029 | 11/1992 | (WO) . |

OTHER PUBLICATIONS

Duan et al. J. Biol. Chem. 266:413–418 (1990).*
Bowie et al. (1990) Science 247:1307–1310.*
Himmler et al. (1990) DNA and Cell Biology 9:705–715, 1990.*
Raines et al. (1991) Proc. Natl. Acad. Sci. 88:8203–8207, Sep. 1991.*
Callard et al. (1994) The Cytokine Factbook, Academic Press, pp. 3 and 174–178.*
Bricogne, G., "Methods and Programs for Direct–Space Exploitation of Geometric Redundancies," *Acta Cryst.,* 32:832–847 (1976).
Brënger, A.T., "Crystallographic Refinement by Stimulated Annealing," *J. Mol. Biol.,* 203:803–816 (1988).
Burnette, W.N., ""Western Blotting":Electrophoretic Transfer of Proteins from Sodium Dodecyl Sulfate–Polyacrylamide Gels to Unmodified Nitrocellulose and Radiographic Detection with Antibody and Radioiodinated Protein A," *Anal. Biochem.,* 112:195–203 (1981).
Cerretti et al., "Human Macrophage–Colony Stimulating Factor: Alternative RNA and Protein Processing From a Single Gene," *Molecular Immunology,* 25(8):761–770, (1988).
Coussens et al., "Structural Alterations of Viral Homologue of Receptor Proto–Oncogene fms at Carboxyl Terminus," *Nature,* 320:277–280 (1986).
Cox, J.M., "Mathematical Methods Used in the Comparison of the Quanternary Structures," (Appendix) *J. Mol. Biol.,* 28:151–156 (1967).
Creighton, T.E., *Proteins: Structural and Molecular Properties,* W.H. Freeman and Co., San Francisco, pp. 79–86 (1983).
Cunningham et al., "Dimerization of the Extracellular Domain of the Human Growth Hormone Receptor by a Single Hormone Molecule," *Science,* 254:821–825 (Nov. 8, 1991).
Fetrow and Bryant, "New Programs for Protein Tertiary Structure Prediction," *Bio/Technology,* 11:479–484 (Apr. 11, 1993).
Gillam et al., "Site–Specific Mutagenesis Using Synthetic Oligodeoxyribonucleotide Primers: I. Optimum Conditions and Minimum Oligodeoxyribonucleotide Length," *Gene,* 8:81–97 (1979).
Halenbeck et al., "Renaturation and Purification of Biologically Active Recombinant Human Macrophage Colony–Stimulating Factor Expressed in *E. coli,*" *Bio/Technology,* 7:710–715 (Jul., 1989).
Home et al., "What is Light," *New Scientist,* 2:30–33 (Nov. 2, 1991).
Luria et al., "Hybridization Between *Escherichia coli* and Shigella," *J. Bact.,* 74:461–476 (1957).
Jancarik et al., "Sparse Matrix Sampling: A Screening Method For Crystallization of Proteins," *J. Appl. Cryst.,* 24:409–411 (1991).

(List continued on next page.)

Primary Examiner—Michael Pak
(74) Attorney, Agent, or Firm—Donald J. Pochopien; Kimberlin L. Morley; Robert P. Blackburn

(57) ABSTRACT

The present invention is directed to methods for crystallizing macrophage colony stimulating factor. The present invention is also directed to methods for designing and producing M-CSF agonists and antagonists using information derived from the crystallographic structure of M-CSF. The invention is also directed to methods for screening M-CSF agonists and antagonists. In addition, the present invention is directed to an isolated, purified, soluble and functional M-CSF receptor.

3 Claims, 8 Drawing Sheets

OTHER PUBLICATIONS

Figure 1:
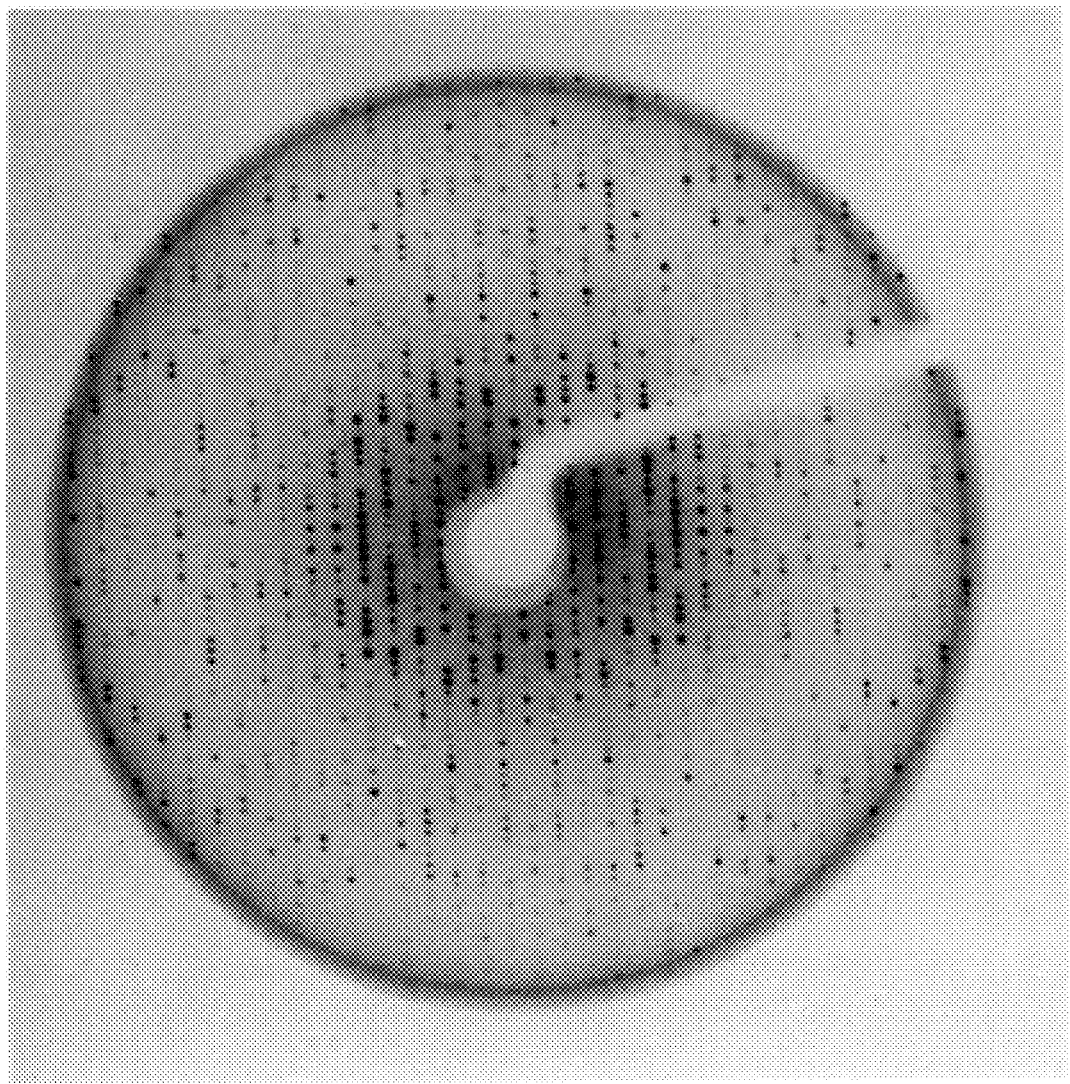

Jones, T.A., "Interactive Computer Graphics: FRODO," *Methods Enzymol.*, 115:157–171 (1985).

Kabsch et al., "Dictionary of Protein Secondary Structure: Pattern Recognition of Hydrogen–Bonded and Geometrical Features," *Biopolymers*, 22:2577–2637 (1983).

Kawasaki et al., "Molecular Cloning of a Complimentary DNA Encoding Human Macrophage–Specific Colony–Stimulating Factor (CSF–1)," *Science*, 230:291–296, (1985).

Ladner et al., "Human CSF–1: Gene Structure and Alternative Splicing of mRNA Precursors," *EMBO J.*, 6:2693–2698, (1987).

Laemmli, U.K., "Cleavage of Structural Proteins during the Assembly of the Head of Bacteriophage T4," *Nature (Canada)*, 227:680–685 (Aug. 15, 1970).

LaLonde et al., "Crystallization and Preliminary X–Ray Studies of Recombinant Human Granulocyte–Macrophage Colony Stimulating Factor," *J. Mol. Biol.*, 205(4):783–785 (1989).

Luckov et al., "Trends in the Development of Baculovirus Expression Vectors," *Bio/Technology*, 6:47–55 (Jan., 1988).

McPherson, A., Preparation and Analysis of Protein Crystals, *A Wiley–Interscience Publication*, John Wiley & Sons, New York, pp. 102–104 (1982).

McPherson, Jr., "Crystallization of Proteins From Polyethylene Glycol," *J. Biol. Chem.*, 251(20):6300–6303 (Oct. 25, 1976).

Metcalf, "Studies on Colony Formation In Vitro by Mouse Bone Marrow Cells," *J. Cell. Physiol.*, 76(1):89–99 (Aug., 1970).

Miles, E.W., "Modification of Histidyl Residues in Proteins by Diethylpyrocarbonate," *Meth Enzymol.*, 47:431–442 (1977).

Mullis et al., "Specific Synthesis of DNA in vitro via a Polymerase–Catalyzed Chain Reaction," *Meth. Enzymol.*, 155:335–350 (1987).

Mullis, K.B., "Specific Enzymatic Amplification of DNA In Vitro: The Polymerase Chain Reaction," *Cold Spring Harbor Symp. on Quant. Biol.* 51:263–273 (1986).

Ollis and White, "Protein Crystallization," Guide to Protein Purification, *Methods in Enzymology*, vol. 182, Deutscher (ed.), Academic Press, Inc., Harcourt Brace Jovanovich, Publishers, San Diego, CA, pp. 646–659 (1991).

Pandit et al., "Three–Dimensional Structure of Dimeric Human Recombinant Macrophage Colony–Stimulating Factor," *Science*, 258:1358–1362 (Nov. 20, 1992).

Ralph et al., "Molecular and Biological Properties of Human Macrophage Growth Factor, CSF–1," *Cold Spring Harbor Symposia on Quantitative Biology*, LI:679–683 (1986).

Ralph et al., "The Molecular and Biological Properties of the Human and Murine Members of the CSF–1 Family" in *Molecular Basis of Lymphokine Action*, Humana Press, Inc., pp. 295–311 (1987).

Ralph et al., "Inducible Production of Human Macrophage Growth Factor, CSF–1," *Blood*, 68:633–639 (1986).

Roberts et al., "Generation of an Antibody With Enhanced Affinity and Specificity for Its Antigen by Protein Engineering," *Nature*, 328:731–734 (Aug. 20, 1987).

Saiki et al., "A Novel Method for the Detection of Polymorphic Restriction Sites By Cleavage of Oligonucleotide Probes: Application to Sickle–Cell Anemia," *Bio/Technology*, 3:1008–10012 (Nov., 1985).

Scopes, R.K., "Crystallization of Proteins," *Protein Purification: Principles and Practice*, Chapter 10 (10.3), Second Edition, Springer–Verlag, pp. 296–321 (1982).

Shadle et al., Human Macrophage Colony–Stimulating Factor Heterogeneity Results From Alternative mRNA Splicing, Deferential Glycosylation, and Proteolytic Processing, *J. Cellular Biochem*, 40:91–107 (1989).

Sporn and Roberts, (eds.), "Peptide Growth Factors and Their Receptors," *Handbook of Experimental Pharmacology*, vol. 1; vol. 95/1, Springer–Verlag, pp. 667–698 (1990).

Stanley et al., "Standardized Bioassay For Bone Marrow Colony Stimulating Factor In Human Urine: Levels in Normal Man," *J. Lab. Clin. Med.*, 79:657–668 (1972).

Van Holde, K.E., "X–Ray Diffraction," *Physical Biochemistry*, Chapter 11, Prentice Hall, N.J. pp. 221–239 (1971).

Wang, B.C., "Resolution of Phase Ambiguity in Macromolecular Crystallography," *Methods Enzymol.*, 115:90–112 (1985).

Ward et al., "Structure of Deoxyhemoglobin A Crystals Grown from Polyethylene Glycol Solutions," *J. Mol. Biol.*, 98:161–177 (1975).

Weber, P.C., "Physical Principals of Protein Crystallization," *Advances in Protein Chemistry*, 41:1–36 (1991).

Yeung et al., "Purification of the Colony Stimulating Factor 1 Receptor and Demonstration of its Tyrosine Kinase Activity," *Proc. Nat'l Acad. Sci., USA*, 84:1268–1271 (Mar., 1987).

* cited by examiner

SEQUENCE LISTING

<160> NUMBER OF SEQ ID NOS: 11

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (H9A, H15A)

<400> SEQUENCE: 1
aggtgtctca tagaaagttc ggacgcaggc cttgtcatgc tcttcataat ccttgg        56

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (H9A, H15A)

<400> SEQUENCE: 2
caggagaaag cttatgtctg aatattgtag cgccatgatt gggagtggag ccctgcag     58

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (H9A)

<400> SEQUENCE: 3
caggagaaag cttatgtctg aatattgtag cgccatgatt gggagtggac acctgcag     58

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (H15A)

<400> SEQUENCE: 4
caggagaaag cttatgtctg aatattgtag ccacatgatt gggagtggag ccctgcag     58

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (Q20A, V78K)

```
<400> SEQUENCE: 5
aggagaaagc ttatgtctga atattgtagc cacatgattg ggagtggaca cctgcagtct    60
ctggctcggc tg                                                        72

<210> SEQ ID NO 6
<211> LENGTH: 85
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (Q20A, V78K)

<400> SEQUENCE: 6
ggacgcaggc cttgtcatgc tcttcataat ccttggtgaa gcagctcttc agcctcaaag    60
agagttcctg cagctgttta atggc                                          85

<210> SEQ ID NO 7
<211> LENGTH: 76
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (Q20A, V78K)

<400> SEQUENCE: 7
catgacaagg cctgcgtccg aactttctat gagacacctc tccagttgct ggcgaaggtc    60
aaggctgtct ttaatg                                                    76

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:Primer
<223> OTHER INFORMATION: Primer for human M-CSF mutant (E115A, N119A)

<400> SEQUENCE: 8
ggatcaggat ccctcggact gcctctc                                        27

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:Primer
<223> OTHER INFORMATION: Human M-CSF

<400> SEQUENCE: 9
gcgtaccatg ggcccaggag ttctgc                                         26

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:Primer
<223> OTHER INFORMATION: Human M-CSF

<400> SEQUENCE: 10
agtcgaggat cctcaatccg ggggatgcgt gtg                                 33
```

```
<210> SEQ ID NO 11
<211> LENGTH: 492
<212> TYPE: PRT
<213> ORGANISM: Artificial Sequence
<220> FEATURE:
<223> OTHER INFORMATION: Description of Artificial Sequence:Primer
<223> OTHER INFORMATION: human soluble M-CSF receptor residues 20 to 511
      (Coussens, L. et al., Nature, 320:277 (1986))

<400> SEQUENCE: 11

Ile Pro Val Ile Glu Pro Ser Val Pro Glu Leu Val Val Lys Pro Gly
  1               5                  10                  15

Ala Thr Val Thr Leu Arg Cys Val Gly Asn Gly Ser Val Glu Trp Asp
                 20                  25                  30

Gly Pro Pro Ser Pro His Trp Thr Leu Tyr Ser Asp Gly Ser Ser Ser
             35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365
```

-continued

```
Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp
                485                 490
```

SOLUBLE EXTRACELLULAR DOMAIN OF HUMAN M-CSF RECEPTOR

This is a continuation of U.S. application Ser. No. 08/351,292 filed May 25, 1995, now U.S. Pat. No. 5,866,114; which is the U.S. national phase of international application PCT/US93/05548 filed on Jun. 9, 1993; which is a continuation-in-part of U.S. application Ser. No. 07/896,512 filed Jun. 9, 1992, now abandoned.

Work described herein was funded with Government support. The Government has certain rights in inventions arising as part of that work.

FIELD OF THE INVENTION

The present invention relates in general to crystalline compositions of macrophage colony stimulating factor "M-CSF" and in particular to methods for the use of structural information (including X-ray diffraction patterns) of crystalline M-CSF for agonist and antagonist production, as well as assays for detection of same.

BACKGROUND OF THE INVENTION

Monocyte-macrophage colony-stimulating factor is produced by a variety of cells, including macrophages, endothelial cells and fibroblasts (see, Ralph et al., "The Molecular and Biological Properties of the Human and Murine Members of the CSF-1 Family" in *Molecular Basis of Lymphokine Action*, Humana Press, Inc., (1987), which is incorporated herein by reference). M-CSF is composed of two "monomer" polypeptides, which form a biologically active dimeric M-CSF protein (hereinafter referred to as "M-CSF dimer"). M-CSF belongs to a group of biological agonists that promote the production of blood cells. Specifically, it acts as a growth and differentiation factor for bone marrow progenitor cells of the mononuclear phagocyte lineage. Further, M-CSF stimulates the proliferation and function of mature macrophages via specific receptors on responding cells. In clinical trials M-CSF has shown promise as a pharmaceutical agent in the correction of blood cell deficiencies arising as a side-effect of chemotherapy or radiation therapy for cancer and may be beneficial in treating fungal infections associated with bone marrow transplants. M-CSF may also play significant biological roles in pregnancy, uveitis, and atherosclerosis. Development of M-CSF agonists or antagonists may prove to be of value in modifying the biological events involved in these conditions.

M-CSF exists in at least three mature forms: short (M-CSFα), intermediate (M-CSFγ), and long (M-CSFβ). Mature M-CSF is defined as including polypeptide sequences contained within secreted M-CSF following amino terminus processing to remove leader sequences and carboxyl terminus processing to remove domains including a putative transmembrane region. The variations in the three mature forms are due to alternative mRNA splicing (see, Cerretti et al. *Molecular Immunology*, 25:761 (1988)). The three forms of M-CSF are translated from different mRNA precursors, which encode polypeptide monomers of 256 to 554 amino acids, having a 32 amino acid signal sequence at the amino terminal and a putative transmembrane region of approximately 23 amino acids near the carboxyl terminal. The precursor peptides are subsequently processed by amino terminal and carboxyl terminal proteolytic cleavages to release mature M-CSF. Residues 1–149 of all three mature forms of M-CSF are identical and are believed to contain sequences essential for biological activity of M-CSF. In vivo M-CSF monomers are dimerized via disulfide-linkage and are glycosylated. Some, if not all, forms of M-CSF can be recovered in membrane-associated form. Such membrane-bound M-CSF may be cleaved to release secreted M-CSF. Membrane associated M-CSF is believed to have biological activity similar to M-CSF, but may have other activities including cell—cell association or activation.

Polypeptides, including the M-CSFs, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, a knowledge of a protein's three-dimensional structure can provide much guidance in designing agents that mimic, inhibit, or improve its biological activity in soluble or membrane bound forms.

The three-dimensional structure of a polypeptide may be determined in a number of ways. Many of the most precise methods employ X-ray crystallography (for a general review, see, Van Holde, *Physical Biochemistry*, Prentice-Hall, N.J. pp. 221–239, (1971), which is incorporated herein by reference). This technique relies on the ability of crystalline lattices to diffract X-rays or other forms of radiation. Diffraction experiments suitable for determining the three dimensional structure of macromolecules typically require high-quality crystals. Unfortunately, such crystals have been unavailable for M-CSF as well as many other proteins of interest. Thus, high-quality, diffracting crystals of M-CSF would assist the determination of its three-dimensional structure.

Various methods for preparing crystalline proteins and polypeptides are known in the art (see, for example, McPherson, et al. "Preparation and Analysis of Protein Crystals", A. McPherson, Robert E. Krieger Publishing Company, Malabar, Fla. (1989); Weber, *Advances in Protein Chemistry* 41:1–36 (1991); U.S. Pat. No. 4,672,108; and U.S. Pat. No. 4,833,233; all of which are incorporated herein by reference for all purposes). Although there are multiple approaches to crystallizing polypeptides, no single set of conditions provides a reasonable expectation of success, especially when the crystals must be suitable for X-ray diffraction studies. Thus, in spite of significant research, many proteins remain uncrystallized.

In addition to providing structural information, crystalline polypeptides provide other advantages. For example, the crystallization process itself further purifies the polypeptide, and satisfies one of the classical criteria for homogeneity. In fact, crystallization frequently provides unparalleled purification quality, removing impurities that are not removed by other purification methods such as HPLC, dialysis, conventional column chromatography, etc. Moreover, crystalline polypeptides are often stable at ambient temperatures and free of protease contamination and other degradation associated with solution storage. Crystalline polypeptides may also be useful as pharmaceutical preparations. Finally, crystallization techniques in general are largely free of problems such as denaturation associated with other stabilization methods (e.g. lyophilization). Thus, there exists a significant need for preparing M-CSF compositions in crystalline form and determining their three-dimensional structure. The present invention fulfills this and other needs. Once crystallization has been accomplished, crystallographic data provides useful structural information which may assist the design of peptides that may serve as agonists or antagonists. In addition, the crystal structure provides information useful to map, the receptor binding domain which could then be mimicked by a small non-peptide molecule which may serve as an antagonist or agonist.

SUMMARY OF THE INVENTION

The present invention provides crystalline forms of M-CSF dimers. Preferably, the dimers are formed from polypeptides containing between 146 to 162 amino acids residues at or near the N-terminus of mature M-CSF (e.g. glu$_1$ glu$_2$ val$_3$ . . . ). In a specific embodiment, the polypeptide includes residues 4 to 158 of mature M-CSFα polypeptide, preferably in the non-glycosylated form.

Another aspect of the invention provides a method of crystallizing an M-CSF. A preferred crystallization method according to the present invention includes the following steps: mixing a preselected, substantially pure M-CSF dimer and a precipitant to form an M-CSF mixture; precipitating crystalline M-CSF from the mixture; and isolating the M-CSF in crystalline form. In some specific embodiments, the precipitant contains polyethylene glycol. Other components such as ammonium sulfate and/or other ionic compounds may be added to the solution. It has been found by x-ray crystallography that M-CSF produced by the method of the present invention can crystallize into the P2$_1$2$_1$2$_1$ space groups for example.

Variations of the crystallization method are also provided. For example, the step of precipitating crystals from the M-CSF mixture may involve equilibrating the M-CSF mixture with a second mixture. The second mixture is typically a solution that consists of a higher concentration of precipitant than the first M-CSF mixture. The step of equilibrating preferably consists of applying the M-CSF mixture to a surface and allowing the applied M-CSF mixture to come into equilibrium with a reservoir of the second mixture. In other embodiments, the step of precipitating M-CSF crystals is initiated by seeding the M-CSF mixture with seed crystals or altering the temperature of the M-CSF mixture. Another aspect of the invention involves identifying compounds that have structures that mimic a receptor binding region of the three-dimensional structure of M-CSF to varying degrees and can in many instances function as M-CSF agonists or antagonists. Compounds that interact with the receptor-binding region of M-CSF may be antagonists. The three-dimensional alpha-carbon coordinates of a truncated M-CSF dimer is presented in Appendix 1. In one embodiment of the present invention, the three-dimensional structure of M-CSF is obtained by first crystallizing an M-CSF dimer (having M-CSF receptor-binding residues) to form at least one M-CSF crystal. Next, a source of radiation is used for irradiating an M-CSF crystal to obtain a diffraction pattern of the M-CSF crystal. Finally, a three-dimensional structure of M-CSF is obtained from the diffraction pattern. In most embodiments, the three-dimensional structure includes an M-CSF receptor-binding region.

Figure 6A:
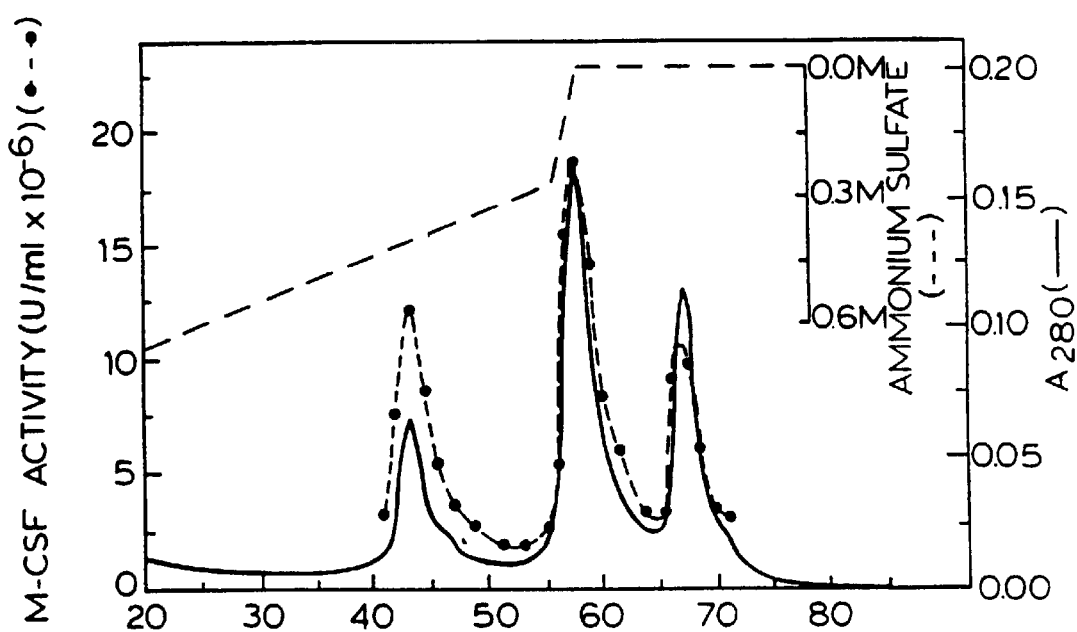
Figure 6B:
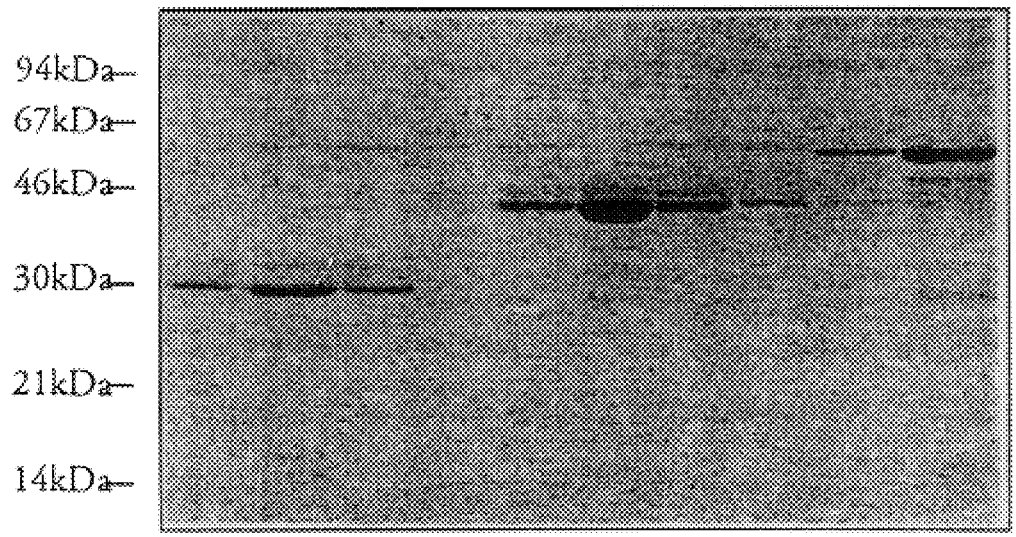
Figure 6C:
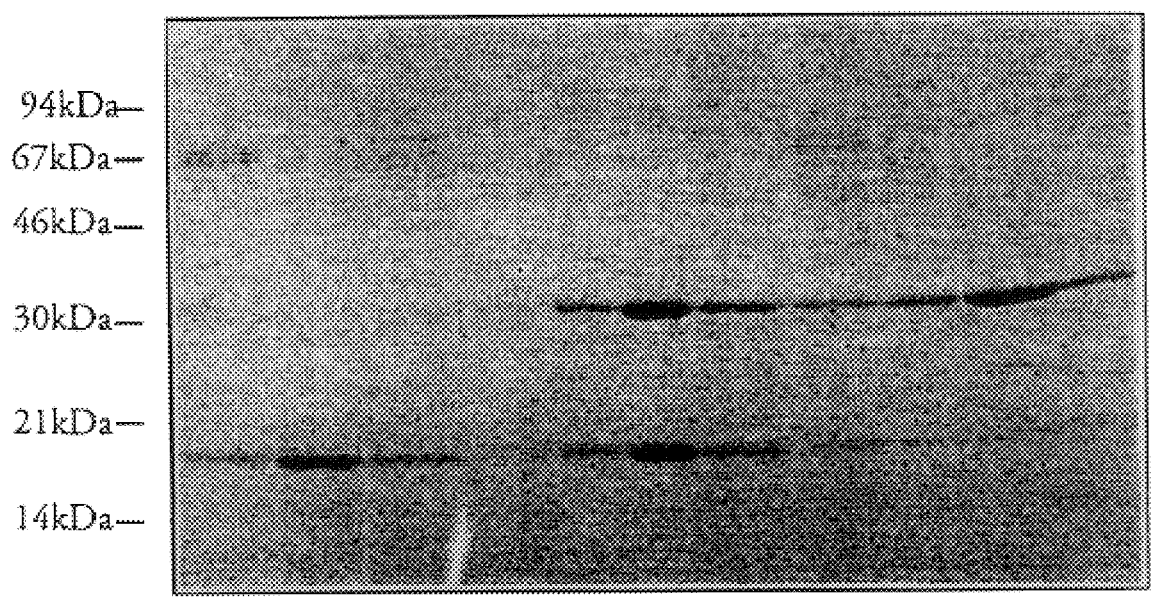
Figure 7:
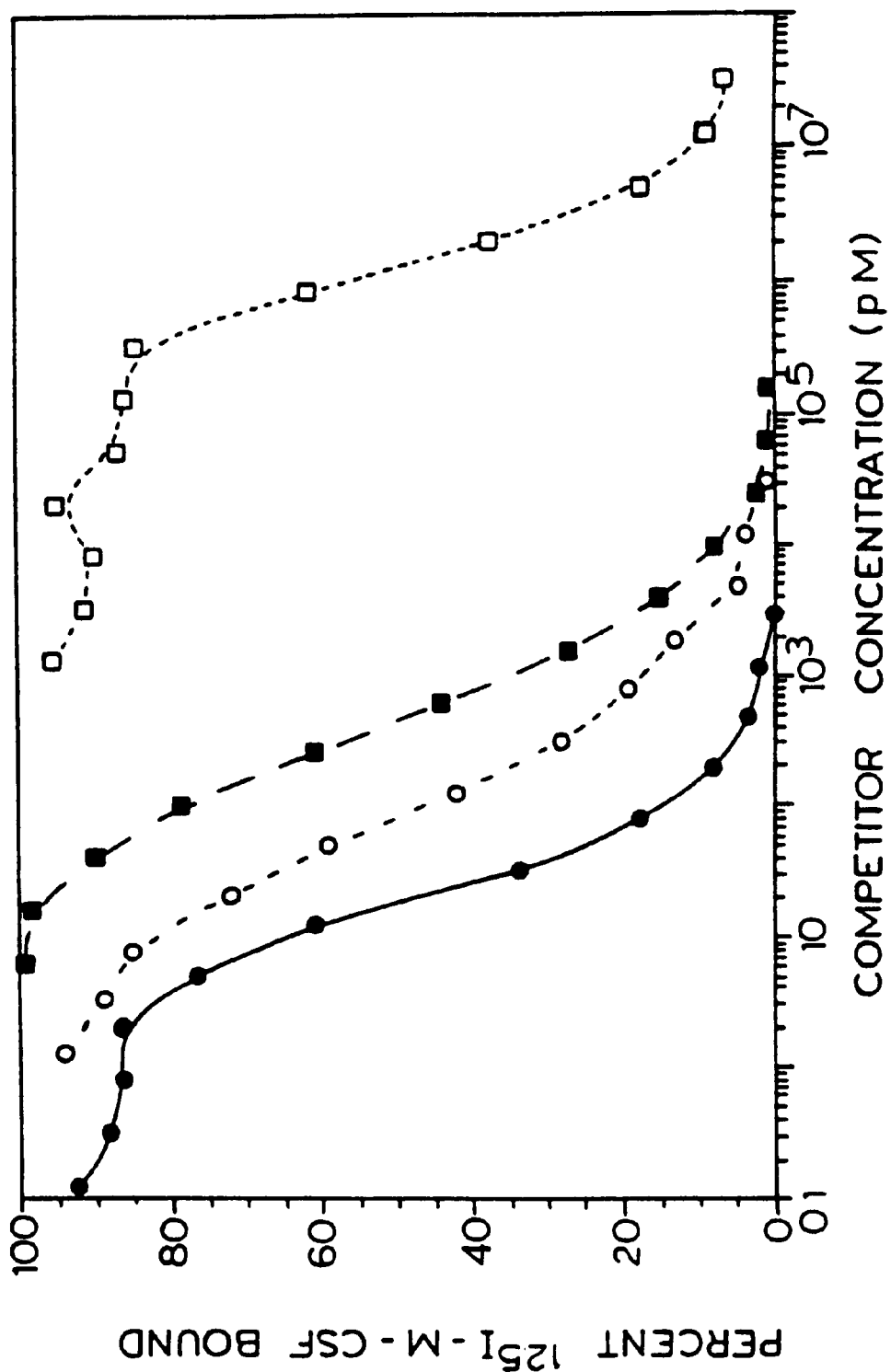

The present invention is also directed to a method for selecting, candidate amino acid substitutions in a protein, based on structural information, and more particularly M-CSF, comprising determining the three-dimensional structure of M-CSF by the methods of the present invention; followed by determining the solvent accessible amino acid residues of the protein, determining which residues are not involved in dimer formation. Applying these criteria, amino acids in M-CSF which are solvent accessible and which are not involved in dimer formation are selected for substitution with non-conservative amino acids. Since M-CSFβ has intrachain disulfide bonds involving cysteines 157 and/or 159, we believe the C-terminal region of M-CSF extends from the "rear" of the structure we have solved, providing a variable-length "tether" for membrane-bound forms of M-CSF. Thus, the "front" or receptor-binding region of M-CSF is on the opposite side of the molecules, consisting of solvent-accessible residues in or near helices A, C, and D, including residues from about 6 to 26, 71 to 90, and 110 to 130, respectively, of native M-CSF. Preferred amino acids for substitution and preferred substituting amino acids include but are not limited to: H15→A or L; Q79→A or D; R86→E or D; E115→A; E41→K or R; K93→A or E; D99→K or R; L55→Q or N; S18→A or K; Q20→A or D; 175→K or E; V78→K or R; L85→E or N; D69→K or R; N70→A or E: H9→A or D; N63→K or R; and T34→Q or K. Most preferred are those substitutions give rise to novel M-CSF agonists and M-CSF antagonists. Additionally, the present invention is also directed to a method for producing antagonists and agonists by substituting at least one and preferably fewer than 5 solvent accessible residues per M-CSF monomer.

The invention is also directed to heterodimeric M-CSF in which only one subunit contains substituted solvent accessible amino acids involved in signal transduction and to heterodimeric M-CSF in which each subunit contains different substituted solvent accessible amino acids involved in signal transduction. The present invention is also directed to M-CSF having amino acid substitutions which do not impair binding to the M-CSF receptor. Screening for agonists and antagonists is then accomplished using bioassays and receptor binding assays using methods well known in the art, including those described in the Examples below.

In addition the invention is directed to an isolated, purified, soluble and functional M-CSF receptor. The present invention is also directed to a method for screening M-CSF agonists and antagonists using a soluble M-CSF receptor.

A further understanding of the present invention can be obtained by reference to the drawings and discussion of specific embodiments.

BRIEF DESCRIPTION OF THE FIGURES

FIG. 1 is a section of a diffraction pattern of an M-CSFα crystal prepared according to the present invention;

FIG. 2 is a topology diagram showing the disulfide bonds in truncated dimeric M-CSF;

FIG. 3 is a stereodiagram of the C-alpha backbone with every tenth residue labelled and with the non-crystallographic symmetry axis indicated by a dotted line;

FIGS. 4A and 4B present two views of a ribbon diagram highlighting the secondary structural elements of M-CSF. The cysteine residues have been represented by a ball-and-stick model and the non-crystallographic symmetry axis is indicated by a dotted line;

FIGS. 5A–5C illustrate size-exclusion HPLC analysis of the NΔ3CΔ158 M-CSF short clone homodimer (158) (FIG. 5A), NΔ3CΔ221 C157S, C159S long clone homodimer (221F) (FIG. 5B), and the short clone/long clone heterodimer (158/221F) (FIG. 5C) and their corresponding biological activities;

FIGS. 6A–6C illustrates size exclusion HPLC(A) and both non-reduced (B) and reduced (C) SDS-PAGE analysis of the preparative purification of M-CSF; more particularly, FIG. 6A graphically illustrates the separation on Phenyl-HPLC size exclusion chromatography of the three species of M-CSF dimers of FIGS. 5A–5C, i.e., the 158 homodimer, the 221F homodimer and the 158/221F heterodimer, and indicates that the three absorbance peaks at 280 nm (solid line) correlate with M-CSF activity in U/ml×$10^{-6}$ (dotted line); FIG. 6B illustrates SDS-PAGE analysis under non-reducing conditions of the preparative purification of the 158/221F heterodimer (intermediate molecular weight species) relative to the 158 homodimer (lower molecular weight species) and the 221F homodimer (highest molecular weight species); FIG. 6C illustrates SDS-PAGE analysis under reducing conditions of the preparative purification of the 158/221F heterodimer (middle lanes) relative to the 158 homodimer (left lanes) and the 221F homodimer (right lanes); and FIG. 7 illustrates the competitive binding of M-CSF and M-CSF muteins to NFS60 cell M-CSF receptors. In FIG. 7, competitive binding curves are shown for M-CSFα NΔ3CΔ158 (closed circles), M-CSFα NΔ3CΔ158 H9A, H15A/M-CSFβ NΔ3CΔ221 C157S, C159S heterodimer (closed squares), dimeric Q20A, V78KF mutein (open circles) and dimeric H9A, H15A mutein (open squares).

DESCRIPTION OF THE PREFERRED EMBODIMENTS DEFINITIONS

As used herein "M-CSF polypeptide" refers to a human polypeptide having substantially the same amino acid sequence as the mature human M-CSFα, M-CSFβ, or M-CSFγ polypeptides described in Kawasaki et al., *Science* 230:291 (1985), Cerretti et al., *Molecular Immunology*, 25:761 (1988), or Ladner et al., *EMBO Journal* 6:2693 (1987), each of which are incorporated herein by reference. Such terminology reflects the understanding that the three mature M-CSFs have different amino acid sequences, as described above.

Certain modifications to the primary sequence of M-CSF can be made by deletion, addition, or alteration of the amino acids encoded by the DNA sequence without destroying the desired structure (e.g., the receptor binding ability of M-CSF) in accordance with well-known recombinant DNA techniques. Further, a skilled artisan will appreciate that individual amino acids may be substituted or modified by oxidation, reduction or other derivitization, and the polypeptide may be cleaved to obtain fragments that retain the active binding site and structural information. Such substitutions and alterations result in polypeptides having an amino acid sequence which falls within the definition of polypeptide "having substantially the same amino acid sequence as the mature M-CSFα, M-CSFβ, and M-CSFγ polypeptides."

For purposes of crystallization, preferred lengths of the M-CSFα, β or γ monomers are between about 145 and 180 amino acids (counting from the mature amino terminus), and more preferably between about 145 and 162 amino acids long. A specific monomer that may be present in a crystallizable dimer is M-CSFα and is NΔ3 M-CSFα CΔ158 (3 amino acids are deleted from the amino terminus and the total length is 155 amino acids). All lengths are inclusive. As used herein the term "M-CSFα (4–158)" denotes an M-CSF having amino acid residues 4 to 158 of the mature, processed M-CSFα polypeptide. Other nomenclature designations for C-terminal and N-terminal truncations of native M-CSF are set forth in U.S. Pat. No. 4,929,700 which is incorporated herein by reference.

Crystallizable glycosylation variants of the M-CSF polypeptides are included within the scope of this invention. These variants include polypeptides; completely lacking in glycosylation and variants having at least one fewer glycosylated site than the mature forms, as well as variants in which the glycosylation pattern has been changed from the native forms. Also included are deglycosylated and unglycosylated amino acid sequence variants, as well as deglycosylated and unglycosylated M-CSF subunits having the mature amino acid sequence (see, U.S. Pat. No. 5,032,626).

"M-CSF" dimer refers to two M-CSF polypeptide monomers that have dimerized. M-CSF dimers may include two identical polypeptide monomers (homodimers) or two different polypeptide monomers (heterodimers such as an M-CSFα-M-CSFβ dimer, an M-CSF long clone and short clone dimer). M-CSF monomers may be converted to M-CSF dimers in vitro as described in U.S. Pat. No. 4,929,700, which is incorporated herein by reference. Recombinantly expressed M-CSFs may also be variably glycosylated as they exist in vivo, partially glycosylated, or completely lacking in glycosylation (unglycosylated). Glycosylated M-CSFs may be produced in vivo with carbohydrate chains which may later be enzymatically deglycosylated in vitro.

Biologically active M-CSF exhibits a spectrum of activity understood in the art. For instance, M-CSF stimulates the proliferation and function of mature macrophages via specific receptors on responding cells. Further, M-CSF acts as a mononuclear phagocyte progenitor growth factor. The standard in vitro colony stimulating assay of Metcalf, *J. Cell Physiol.* 76:89 (1970) (which is incorporated herein by reference) results primarily in the formation of macrophage colonies when M-CSF is applied to stem cells. Other biological assays are based on M-CSF induced proliferation of M-CSF dependent cells such as the NFS-60 cell line. As used herein "M-CSF having biological activity" refers to M-CSF, including fragments and sequence variants thereof as described herein; that exhibit an art-recognized spectrum of activity with respect to biological systems. Such M-CSF having biological activity will typically have certain structural attributes in common with those of the mature M-CSF forms such as receptor binding site tertiary structure.

Agonists are substances that exhibit greater activity per se than the native ligand while antagonists are substances that suppress, inhibit, or interfere with the biological activity of a native ligand. Agonists and antagonists may be produced by the methods of the present invention for use in the treatment of diseases in which M-CSF has been implicated either as a potential treatment (e.g., for treating blood cell deficiencies arising as a side effect of chemotherapy treating fungal infection associated with bone marrow transplants and others) or as having a role in the pathogenesis of the disease (e.g., ovarian cancer, uveitis, atherosclerosis).

Crystallization of M-CSF species in accordance with the present invention includes four general steps: expression, purification, crystallization and isolation.

Expression of Recombinant M-CSF

M-CSF crystallization requires an abundant source of M-CSF that may be isolated in a relatively homogeneous form. A variety of expression systems and hosts are suitable for the expression of M-CSF and will be readily apparent to one of skill in the art. Because of the variability of glycosylation and other post-transnational modifications present in M-CSF produced in certain eukaryotic hosts, expression in *E. coli* may provide M-CSF with advantageous properties with regard to crystallization. Typical in vitro M-CSF expression systems are described in U.S. Pat. No. 4,929,700, for example.

For use in the present invention, a variety of M-CSF polypeptides can also be readily designed and manufactured utilizing recombinant DNA techniques well known to those skilled in the art. For example, the M-CSF amino acid sequence can vary from the naturally occurring sequence at the primary structure level by amino acid substitutions, insertions, deletions, and the like. These modifications can be used in a number of combinations to produce the final modified polypeptide chain. The present invention is useful for crystallizing such polypeptides and dimers thereof.

In general, modifications of the genes encoding the M-CSF polypeptide are readily accomplished by a variety of well-known techniques, such as site-directed mutagenesis (see, Gillman and Smith, *Gene* 8:81–97 (1979) and Roberts, S. et al., *Nature* 328:731–734 (1987) and U.S. Pat. No. 5,032,676, all of which are incorporated herein by reference). Most modifications are evaluated by screening in a suitable assay for the desired characteristic. For instance, a change in the M-CSF receptor-binding character of the polypeptide can be detected by competitive assays with an appropriate reference polypeptides or by the bioassays described in U.S. Pat. No. 4,847,201, which is incorporated herein by reference.

Insertional variants of the present invention are those in which one or more amino acid residues are introduced into a predetermined site in the M-CSF. For instance, insertional variants can be fusions of heterologous proteins or polypeptides to the amino or carboxyl terminus of the subunits. Substitutional variants are those in which at least one residue has been removed and a different residue inserted in its place. Nonnatural amino acids (i.e., amino acids not normally found in native proteins), as well as isosteric analogs (amino acid or otherwise) are also suitable for use in this invention. Examples of suitable substitutions are well known in the art, such as the Glu→Asp, Ser→Cys, and Cys→Ser, His→alanine for example. Another class of variants are deletional variants, which are characterized by the removal of one or more amino acid residues from the M-CSF.

Other variants of the present invention may be produced by chemically modifying amino acids of the native protein (e.g., diethylpyrocarbonate treatment which modifies histidine residues). Preferred or chemical modifications which are specific for certain amino acid side chains. Specificity may also be achieved by blocking other side chains with antibodies directed to the side chains to be protected Chemical modification includes such reactions as oxidation, reduction, amidation, deamidation, or substitution of bulky groups such as polysaccharides or polyethylene glycol (see e.g., U.S. Pat. No. 4,179,337 and WO91/21029 both of which are incorporated herein by reference).

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; and transaminase-catalyzed reaction with glyoxylate, and N-hydroxysuccinamide esters of polyethylenene glycol or other bully substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified with particular interest in, introducing spectral labels into tyrosyl residues by reaction with aromatic diazonium compounds or tetranitromethane are used to form O-acetyl tyrosyl species and 3-nitro derivatives, respectively. Tyrosyl residues may also be iodinated using $^{125}I$ or $^{131}I$ prepare labeled proteins for use in radioimmunoassay.

Carboxyl side groups (aspartyl or glutamyl) may be selectively modified by reaction with carbodiimides (R—N=C=N—R$^1$), where R and R$^1$ are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Conversely, glutaminyl and asparaginyl residues may be deamidated to the corresponding glutamyl and aspartyl residues, respectively, under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group.

The availability of a DNA sequence encoding M-CSF permits the use of various expression systems to produce the desired polypeptides. Construction of expression vectors and recombinant production from the appropriate DNA sequences are performed by methods well known in the art. These techniques and various other techniques are generally performed according to Sambrook et al., *Molecular Cloning— A Laboratory Manual,* Cold Spring Harbor Laboratory, Cold Spring Harbor, N.Y. (1989), and Kriegler, M., *Gene Transfer and Expression, A Laboratory Manual,* Stockton Press, New York (1990), both of which are incorporated herein by reference.

Purification of M-CSF

Purification steps are employed to ensure that the M-CSF is isolated, prior to crystallization, in a relatively homogeneous state. In general, a higher purity solution increases the likelihood of success of subsequent crystallization steps. Typical purification methods include the use of centrifugation, partial fractionation using salt or organic compounds, dialysis, conventional column chromatography (such as ion-exchange, molecular sizing chromatography etc.), high performance liquid chromatography (HPLC), and gel electrophoresis methods (see, e.g., Deutcher. "Guide to Protein Purification" in *Methods in Enzymology* (1990), Academic Press, Berkely, Calif., which is incorporated herein by reference for all purposes). Preferred purification conditions for generating unusually homogeneous M-CSF species as well as purification of these species are disclosed, for example, in U.S. Pat. No. 4,929,700 which is incorporated herein by reference. Other purification methods are known and will be apparent to one of skill in the art.

Crystallization of M-CSF

Although many of the same physical principles govern crystallization of polypeptides (including M-CSF dimers) and small molecules, the actual crystallization mechanisms differ significantly. For example, the lattice of small-molecule crystals effectively excludes solvent while that of polypeptide crystals includes substantial numbers of solvent molecules. Thus, special techniques must typically be applied to crystallize polypeptides.

Polypeptide crystallization occurs in solutions where the polypeptide concentration exceeds its solubility maximum (i.e., the polypeptide solution is supersaturated). Such "thermodynamically metastable" solutions may be restored to equilibrium by reducing the polypeptide concentration, preferably through precipitation of the polypeptide crystals.

Often polypeptides may be induced to crystallize from supersaturated solutions by adding agents that alter the polypeptide surface charges or perturb the interactions between the polypeptide and bulk water to promote associations that lead to crystallization.

Compounds known as "precipitants" are often used to decrease the solubility of the polypeptide in a concentrated solution. Precipitants induce crystallization by forming an energetically unfavorable precipitant depleted layer around the polypeptide molecules. To minimize the relative amount of this depletion layer, the polypeptides form associations and ultimately crystals as explained in Weber, *Advances in Protein Chemistry* 41:1–36 (1991) which was previously incorporated by reference, In addition to precipitants, other materials are sometimes added to the polypeptide crystallization solution. These include buffers to adjust the pH of the solution (and hence surface charge on the peptide) and salts to reduce the solubility of the polypeptide. Various precipitants are known in the art and include the following: ethanol, 3-ethyl-2,4-pentanediol; and many of the polyglycols, such as polyethylene glycol. A suitable precipitant for crystallizing M-CSF is polyethylene glycol (PEG), which combines some of the characteristics of the salts and other organic precipitants (see, for example, Ward et al., *J. Mol. Biol.* 98:161 [1975] which is incorporated herein by reference for all purposes and McPherson *J. Biol. Chem.* 251:6300 [1976], which was previously incorporated by reference).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the polypeptide and precipitant concentrations thereby causing the polypeptide to reach supersaturation levels.

In the hanging drop technique, an initial polypeptide mixture is created by adding a precipitant to concentrated polypeptide solution. The concentrations of the polypeptide and precipitants are such that in this initial form, the polypeptide does not crystallize. A small drop of this mixture is placed on a glass slide which is inverted and suspended over a reservoir of a second solution. The system is then sealed. Typically the second solution contains a higher concentration of precipitant or other dehydrating agent. The difference in the precipitant concentrations causes the protein solution to have a higher vapor pressure than the solution. Since the system containing the two solutions is sealed, an equilibrium is established, and water from the polypeptide mixture transfers to the second solution. This equilibration increases the polypeptide and precipitant concentration in the polypeptide solution. At the critical concentration of polypeptide and precipitant, a crystal of the polypeptide will form. The hanging drop method is well known in the art (see, McPherson *J. Biol. Chem.* 251:6300 [1976], which was previously incorporated herein by reference).

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

In preferred embodiments, the crystals of the present invention will be formed from a dimer of M-CSF polypeptides. Preferred crystals are typically at least about 0.2×0.2× 0.05 mm, more preferably larger than 0.4×0.4×0.4 mm, and most preferably larger than 0.5×0.5×0.5 mm. After crystallization, the protein may be separated from the crystallization mixture by standard techniques.

The crystals so produced have a wide range of uses. For example, high quality crystals are suitable for X-ray or neutron diffraction analysis to determine the three-dimensional structure of the M-CSF and, in particular, to assist in the identification of its receptor binding site. Knowledge of the binding site region and solvent-accessible residues available for contact with the M-CSF receptor allows rational design and construction of agonists and antagonist for M-CSFs. Crystallization and structural determination of M-CSF muteins having altered receptor binding ability or bioactivity allows the evaluation of whether such changes are caused by general structural deformation or by side chain alteration at the substitution site:.

In addition, crystallization itself can be used as purification method. In some instances, a polypeptide or protein will crystallize from a heterogeneous mixture into crystals. Isolation of such crystals by filtration, centrifugation, etc. followed by redissolving the polypeptide affords a purified solution suitable for use in growing the high-quality crystals necessary for diffraction studies. These high-quality crystals may also be dissolved in water and then formulated to provide an aqueous M-CSF solution having various uses known in the art including pharmaceutical purposes.

Of course, amino acid sequence variants of M-CSF may also be crystallized and used. These mutants can be used for, among other purposes, obtaining structural information useful for directing modification of the binding affinity for M-CSF receptors. As with the naturally occurring forms, the modified M-CSF forms may be useful as pharmaceutical agents for stimulating bone marrow proliferation, overcoming immune suppression and fungal diseases induced by chemotherapy, improving therapeutic efficacy, and lessening the severity or occurrence of side effects during therapeutic use of the present invention. Furthermore, modified M-CSFs may be useful for treatment of disease in which soluble or membrane-bound M-CSF causes or exacerbates the disease state.

Characterization of M-CSF

After purification, crystallization and isolation, the subject crystals may be analyzed by techniques known in the art. Typical analysis yield structural, physical, and mechanistic information about the peptides. As discussed above, X-ray crystallography provides detailed structural information which may be used in conjunction with widely available molecular modeling programs to arrive at the three-dimensional arrangement of atoms in the peptide. Exemplary modeling programs include "Homology" by Biosym (San Diego, Calif.), "Biograf" by BioDesign, "Nemesis" by Oxford Molecular, "SYBYL" and "Composer" by Tripos Associates, "CHARM" by Polygen (Waltham, Mass.), "AMBER" by University of California, San Francisco, and "MM2" and "MMP2" by Molecular Design, Ltd.

Peptide modeling can be used to design a variety of agents capable of modifying the activity of the subject peptide. For example, using the three-dimensional structure of the active site, agonists and antagonists having complementary structures can be designed to enhance the therapeutic utility of M-CSF treatment or to block the biological activity of M-CSF. Further, M-CSF structural information is useful for directing design of proteinaceous or non-proteinaceous M-CSF agonists and antagonists, based on knowledge of the contact residues between the M-CSF ligand and its receptor. Such residues are identified by the M-CSF crystal structure as those which are solvent-accessible, distal to the carboxyl terminal membrane anchoring region not involved in dimer interface stabilizations, and possibly including residues not conserved between human and mouse M-CSF (which does not recognize the human M-CSF receptor).

EXAMPLE 1

Systematic crystallization trials with M-CSF were made using the hanging drop technique. A microdroplet (5 µl) of mother liquor is suspended from the underside of a microscope cover slip, which is placed over a well containing 1 ml of the precipitating solution. 60–70 initial trials were set up, in which pH, temperature, counterion and precipitant were varied. From these trials, the few that gave promising microcrystals were picked for more careful examination.

It was discovered that suitable crystals may be grown from a 20 µl drop containing: 10 mg/ml protein, 100 mM $MgCl_2$, 50 mM Tris.Cl, pH 8.5, and 12% PEG 4000. This drop was equilibrated against a reservoir containing 24% PEG 4000. Tiny, needle-like crystals appeared in 2–3 days which were redissolved in 10 µl water and recrystallized at room temperature. Good quality chunky crystals appeared in 7–9 days in sizes ranging from 0.3×0.3×0.3 mm to 0.5×0.5× 1.0 mm.

Precession photographs revealed the space group to be $P2_12_12_1$ with unit cell dimensions: a=33.53 Å, b=65.11 Å, c=159.77 Å. This gives a unit cell volume of 349084.5 Å$^3$, which is consistent with a dimer in the crystallographic asymmetric unit, and 52% of the unit cell volume being occupied by solvent. The crystals diffracted to a resolution of 3 Å on a Rigaku rotating anode X-ray generator (Danvers, Mass.) operated at 50 kV and 60 mA, and to 2.6 Å in synchrotron radiation.

Screening for heavy atom derivatives was done by soaking crystals into solutions of heavy-metal salts. Zero-level precession pictures of the soaks were used to identify potential derivatives. About 30 different soaking conditions were examined, of which 4 potential derivatives were identified. Unfortunately, some soaks caused the crystals to exhibit non-isomorphism (i.e., the heavy atom soaks induced a change in cell dimensions, making them unusable for phase calculation).

Three-dimensional intensity data were collected on film using an oscillation camera on the X-ray beam-line at the National Synchrotron Light Source, Brookhaven. Several other data sets, of native (underivatized M-CSF) as well as potential derivative crystals have been collected on a Rigaku X-ray generator. The following data sets were collected.

| Crystal | Resolution (Å) | N (observations) | N (unique) | X-Ray Source |
|---|---|---|---|---|
| Native | 2.8 | 27922 | 7311 | Synchrontron |
| Native | 2.9 | 35236 | 7002 | Rigaku (film) |
| Native | 3.5 | 5144 | 5116 | Rigaku (diffractometer) |
| $K_2Hg(SCN)_4$ | 3.5 | 15885 | 4119 | Rigaku (film) |
| $UO_2Cl_2$ | 3.5 | 25492 | 5048 | Rigaku (film) |
| Cis-Pd(NH$_3$)$_2$Cl$_2$ | 3.1 | 26122 | 6304 | Synchrotron |

EXAMPLE 2

Recombinant M-CSF polypeptides were purified from *E. coli*. and renatured to form a disulfide-linked dimeric protein as described in U.S. Pat. No. 4,929,700. Crystallization of the resulting unglycosylated M-CSFα protein (amino acids 4–158 in homodimeric form) was performed by the hanging drop method. Glass microscope plates were siliconized prior to use by dipping immersion into a 1% (volume:volume) solution of the organosilane compound, Prosil-28 (PCR Incorporated, Gainesville, Fla., 32602) washing the treated glass plates with water, and baking at 180 degrees.

A 2 mg/ml aqueous solution of purified human recombinant M-CSF was dialyzed and concentrated against 50 mM Tris-HCl (pH 8.5) using a dialysis tubing having a 10 kD cutoff. The final concentration of polypeptide (10 mg/ml) was determined by ultraviolet spectrophotometry at 280 nm.

About 7 microliters of the concentrated solution was mixed in each well of the spot plate with 7 microliter of 20% (v/v) PEG 4000, 0.2 M $MgCl_2$, 0.1 M Tris-HCl (pH 8.5). The spot plate was then placed in a clear plastic sandwich box containing 20 ml of 23% PEG 4000, 0.2 M $MgCl_2$, 0.1 M Tris-HCl (pH 8.5) and the box was immediately sealed and stored at room temperature. Minor variations in this procedure such as altering buffer conditions are within the scope of the present invention. For example, in a preferred embodiment of the present invention, buffer conditions were altered to include 150 mM $MgCl_2$ and 24% PEG 4000.

After 3–5 days, small microcrystals having a size of 0.1×0.1×0.05 mm appeared in each well. These microcrystals were isolated and redissolved in 25 microliter of 50 mM Tris-HCl and allowed to stand at room temperature. The purified M-CSF crystallized from solution into large hexagonal prism shaped crystals ranging in size from 0.3×0.3× 0.3 mm to 1 mm×2 mm×0.5 mm. These crystals were stable at room temperature for at least three months. In some instances, an artificial mother liquor was prepared using 23% PEG 4000 and 150 mM $MgCl_2$ crystals were then added to this mother liquor. In these cases, the crystals were removed from the mother liquor immediately prior to analysis.

Using reducing and non-reducing SDS-PAGE analysis, the M-CSF in the crystals was shown to be identical in molecular weight to the biologically active starting material. Thus, the M-CSF structure obtained from the crystals is likely to be essentially identical to the structure of biologically active M-CSF.

EXAMPLE 3

Glass microscope slides were prepared as described in Example 2. 7 microliters of the same concentrated M-CSFα protein solution was mixed in each well of the spot plate with 7 microliter of 30% (v/v) PEG 4000, 0.2 M ammonium acetate, 0.1 M acetate buffer (pH 7.5). The spot plate was then placed in a clear plastic sandwich box containing 20 ml of 30% PEG 4000, 0.2 M ammonium acetate, 0.1 M acetate buffer (pH 7.5) and the box was immediately sealed and stored at room temperature. After 3–5 days, thin, plate-like, fragile crystals having a size of approximately 0.3×0.3×0.05 mm appeared.

EXAMPLE 4

Preliminary X-ray Analysis

X-ray crystallographic analysis using precession photographs showed that the crystals produced in Example 2 have an orthorhombic crystal lattice in the $P2_12_12_1$ space group with cell dimensions a=33.54, b=65.26, c=159.63 d=90.0, e=90.0 and f=90.0 angstroms and diffract to a nominal resolution of 2.6 angstroms using synchrotron radiation.

These data provided a unit cell volume of 348084.5 angstroms$^3$, which is consistent with a dimer in the crystallographic asymmetric unit with 52% of the unit cell volume being occupied by solvent. FIG. 1 is a 12-degree precession photograph of the Ok1-zone section of the M-CSF crystal. The photograph was taken using a precession camera manufactured by Enraf-Nonius Company (Delft, Holland), mounted on a Rigaku RU-200 X-ray generator operated at 50 kV and 50 mA.

EXAMPLE 5

Testing of M-CSF Receptor Binding Ability Using Soluble M-CSF Receptor

An essential step in the biological function of M-CSF in vivo is the binding to the M-CSF receptor, also referred to as the c-fms gene product. Recombinant human soluble M-CSF receptor (rhsM-CSFR), representing amino acids; 20 to 511 SEQ ID NO:11 (Coussens, L et al., *Nature*, 320:277 (1986)) was used as an in vitro assay reagent to test the receptor-binding ability of M-CSF proteins. To generate a soluble form of the transmembrane receptor, only the extracellular domain of the human M-CSF receptor was expressed in a baculovirus/insect cell recombinant expression system. In order to purify the soluble receptor without adversely effecting tertiary or quaternary structure, non-denaturing chromatographic methods were chosen, as described below. Other choices exist for the purification of the recombinant receptor. Affinity chromatography may be employed when either a suitable antibody to or ligand for the receptor are available. Alternatively, "tags" may be added to the C-terminus of the recombinant receptor, i.e., KT3 antibody recognition sequence, and purified by an anti-tag antibody, i.e., KT3, column, for use in affinity chromatography. In expression systems in which the rhsM-CSFR is glycosylated, lectin chromatography can be used to enrich for specific glycoproteins.

The rhsM-CSFR can be used to study ligand/receptor interactions as well as ligand-induced receptor dimerization. The assay used to detect ligand/receptor binding employed the use of size exclusion-HPLC, essentially as described in European Patent Application WO92/21029, C. Cunningham, et al., with the following modifications: the column used was a Superose 6 (Pharmacia LKB Biotechnology, Inc.) and the mobile phase was PBS at 0.5 ml/min and a M-CSF to rhsM-CSFR ratio of 1:2. At this ratio, the M-CSF/rhsM-CSFR complex chromatographed with an apparent hydrodynamic radius of 190,000 molecular weight, the molecular weight expected for a M-CSF(rhsM-CSFR)$_2$ complex. Other assays may be employed to measure ligand/receptor binding or receptor dimerization such as chemical crosslinking and SDS-PAGE or immunoprecipitation and SDS-PAGE. Molecules that inhibit receptor dimerization but not ligand binding provide another method to antagonize M-CSF actions.

The DNA encoding rhsM-CSFR was cloned for expression in insect cells using the following general strategy. The portion of the c-fms gene corresponding to amino acids one to 511 was amplified from human macrophage cDNA by polymerase chain reaction (PCR) using an upstream primer of: 5'-GCGTA<u>CCATGG</u>GCCCAGGAGTTCTGC-3' (SEQ ID NO. 9) and a downstream primer of: 5'-AGTCGA<u>GGATCC</u>TCAATCCGGGGATGCGTGTG-3' (SEQ ID NO. 10). The underlined sequences are the NcoI and BamHI restriction sites used to subclone the PCR product into the pAcC5 vector (Luckov et al., *Bio/Technology* 6:47–55). The pAcC5:hsM-CSFR vector was expressed in SF9 insect cells using a baculovirus helper vector as previously described (Summers, et al., *A Manual of Methods for Baculovirus Vectors and Insect Cell Culture Procedures* (1987)).

Approximately two liters of serum-free 72-hour conditioned medium was collected by centrifugation and filtration from SF9 cells infected with pAcC5:hsM-CSFR construct described above. The material was diafiltered with DEAE buffer A [10 mM Tris, pH 8.8, containing the following protease inhibitors (which were added all buffers throughout the purification): 1 mM EDTA, 2 µg/ml leupeptin and 100 µM PMSF] and concentrated 20-fold with a 20,000 molecular weight cutt-off Pyrostat Ultrafiltration Membrane (Sartorius). The retentate was loaded onto a DEAE Sepharose column (Pharmacia LKB Biotechnology, Inc., Piscataway, N.J.) having a bed volume of 100 ml that had been pre. equilibrated with DEAE Buffer A. Elution was at 5 ml/min with a 0–0.8 M NaCl gradient in 500 ml of DEAE Buffer A. Fractions enriched in rhsM-CSFR were detected Western Analysis [Burnett, R., *Anal. Biochem.*, 112:195 (1981)] and dot blot analysis of serially diluted fractions, using anti-c-fms monoclonal antibodies (Oncogene Sciences, Inc.). The dot blot assay was used throughout the purification to identify fractions containing rhsM-CSF. Enriched fractions were pooled, made 0.8 M in ammonium sulfate, adjusted to pH 7.0 and loaded onto a Phenyl TSK-5-PW HPLC column (7.5×75 mm) (BioRad). The column was eluted at 1 ml/min with a decreasing ammonium sulfate gradient over 45 minutes, peak fractions were pooled and concentrated 10-fold with a stir cell concentrator using a YM30 membrane (Amicon). The retentate was chromatographed with FG3000XL size exclusion column (DU PONT, Wilmington, Del.) using a mobile phase a phosphate-buffered saline (PBS) at 3 ml/min. The purified receptor was pooled, concentrated to 1 mg/ml as above and stored at 4° C. This process recovered 650 µg of rhsM-CSFR, purified 200-fold. The preparation was about 95% homogeneous as assayed by SDS-PAGE stained with Coomassie Blue.

EXAMPLE 6

Crystallization of M-CSF/Soluble M-CSF Receptor Complex

To crystallize the M-CSF/rhsM-CSFR complexes, glass microscope slides are prepared as described in Example 2. The M-CSF composition used is incubated with a purified soluble form of the M-CSF receptor, truncated at a residue before the transmembrane region, to form an M-CSF/receptor complex. In certain cases, the rhsM-CSFR is deglycosylated prior to the size exclusion step by incubation with N-glycanase (Genzyme, Cambridge Mass.) according to the manufacturer's instructions. A small quantity of M-CSF/receptor solution is mixed in each well of the spot plate with a comparable quantity of a drop solution (such as about 20% (v/v) PEG 4000, 0.2 M MgCl$_2$, 0.1 M Tris-HCl (pH 8.5)). The spot plate is then placed in a clear plastic sandwich box containing a small amount of precipitant solution (such as about 23% PEG 4000, 0.2 M MgCl$_2$, 0.1 M Tris-HCl (pH 8.5)). The box is immediately sealed and stored at room temperature.

After a few days, crystalline M-CSF-receptor complex is isolated and redissolved in a solution containing about 50 mM Tris-HCl and is allowed to stand at room temperature. The purified M-CSF-receptor complex crystallizes from solution to form crystals for X-ray structural analysis. To facilitate solution of the crystal structure of such complexes, truncated, non-glycosylated forms of the rhsM4-CSFR (described above) which retain M-CSF binding ability may be employed to generate M-CSF-receptor complex crystals.

EXAMPLE 7

The biological activity of the non-glycosylated, truncated sequence used in Examples 2 and 3 was shown to be equal to that of the mature protein purified from human urine (Halenbeck, R., et al., *Bio/Technology*, 7:710–715 [1989]). As noted, the resulting crystals had an orthorhombic crystal lattice in the $P2_12_12_1$ space group, with cell dimensions a=33.54, b=65.26, and c=159.63 Å. Intensity data were collected using imaging plates mounted on a Weissenberg camera modified for macromolecular crystallography at the Photon Factory in Tsukuba, Japan. Native data to a nominal resolution of 2.0 Å, and mercury and platinum derivative data were collected using 1.0 Å radiation. Two crystal settings were used to collect native data [Rmerge (I)=7.0%, using all measurements with I>0.0].

Heavy atom derivatives of M-CSF crystals were prepared by soaking crystals in heavy atom compounds dissolved in the reservoir solution. Isomorphous and anomalous difference Patterson maps clearly revealed one site for the mercury and two sites for the platinum derivative. Anomalous and isomorphous phase information as used in initial phase refinement with the PROTEIN program package. The final figure of merit was 0.62 (8.0–3.0 Å, 6960 reflections). After solvent flattening, B. C. Wang, *Methods Enzymol*, 115:90 (1985), two bundles of four alpha helices related by an approximate two-fold axis could be seen in the electron density map. Rotation and translation parameters of this non-crystallographic axis were refined by a density correlation method, J. M. Cox, *J. Mol. Biol.* 28:151 (1967). Phases were then iteratively refined by molecular averaging and solvent flattening, G. Bricogne, *Acta Cryst.*, 32:832 (1976), using an envelope calculated by putting 5 Å spheres around all the atoms in the four helical bundle. Chain racing and model building were done in the resulting map, (using the program FRODO), T. A. Jones, *Methods Enzymol.* 115:157 (1985), keeping the original MIR map as a reference.

The starting partial model for refinement contained only a polyalanine backbone for eight helices making up the two bundles. Positional refinement using the program XPLOR, A. T. Brunger, *J. Mol. Biol.* 203:803 (1985), gave an R-factor of 0.49 to 3.0 Å. Phase combination with the refined MIR phases resulted in a map of sufficient quality to allow the tracing of two long loops traversing the four helical bundle and a short loop connecting two of the helices. Two strong peaks in the density, one at the top of the first helix, and the second lying directly on the molecular two fold axis, were assigned as disulfide bonded cysteines. The number of residues between these two peaks uniquely identified the position in the sequence of these cysteines and consequently the sequence of the intervening residues. This initial registration was confirmed by the presence of a number of regions of strong density corresponding to aromatic side chains in the sequence. Partial model phase combination using the added loops and those side chains that were visible allowed the remaining residues to be registered, thus determining the overall topology of the molecule. The presence of seven disulfide bonds in the dimer served as important "tether points" to confirm the correctness of the tracing.

Figure 2:
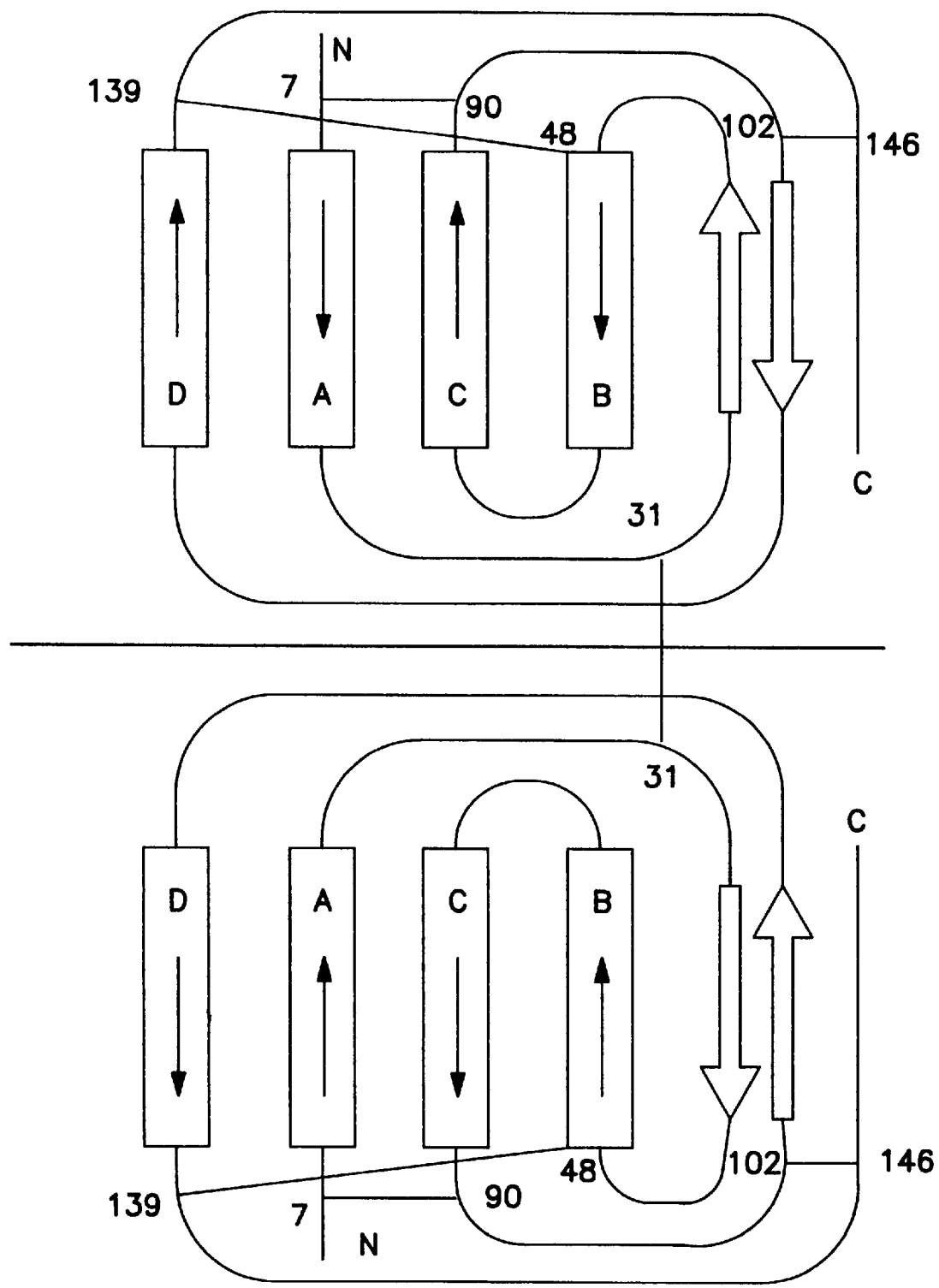

As shown in FIG. 2, the overall topology of this form of M-CSF is that of an antiparallel four α-helical bundle, in which the helices run up-up-down-down, unlike the more commonly observed up-down-up-down connectivity of most four helical bundles. A long crossover connection links helix A to helix B and a similar connection is found between helices C and D.

Figure 3:
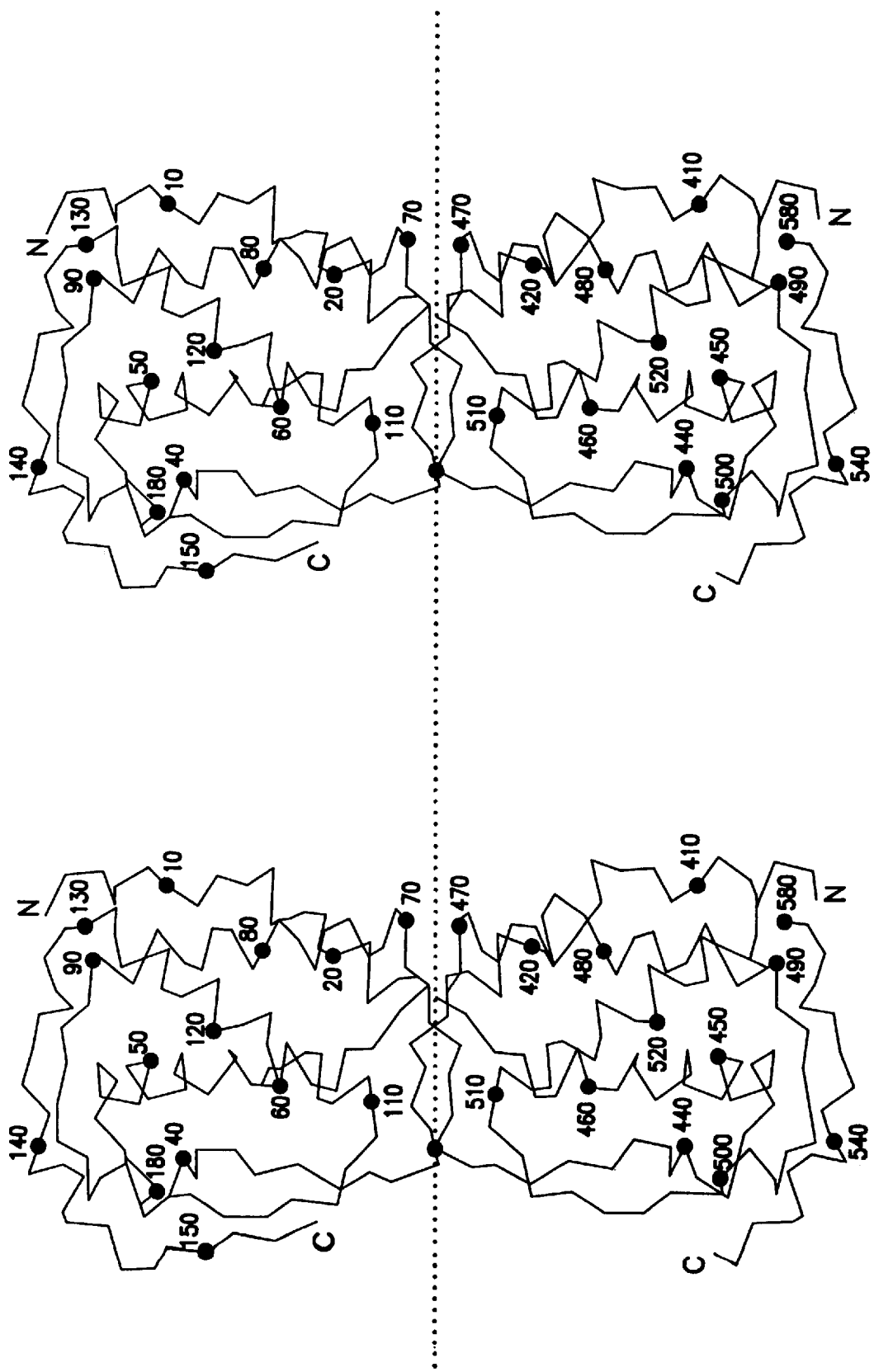
Figure 4A:
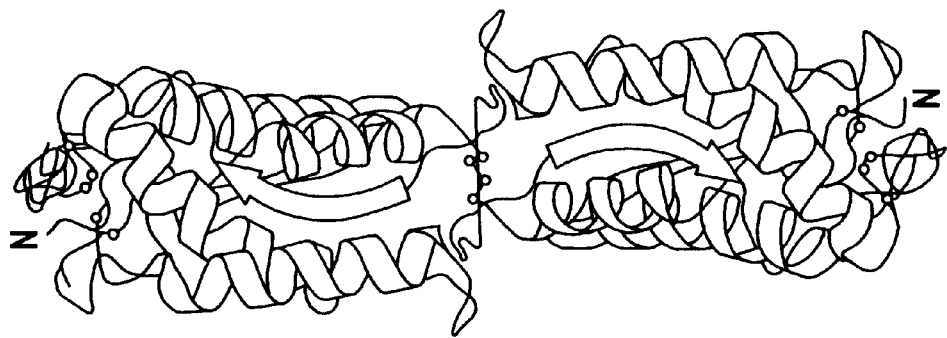
Figure 4:
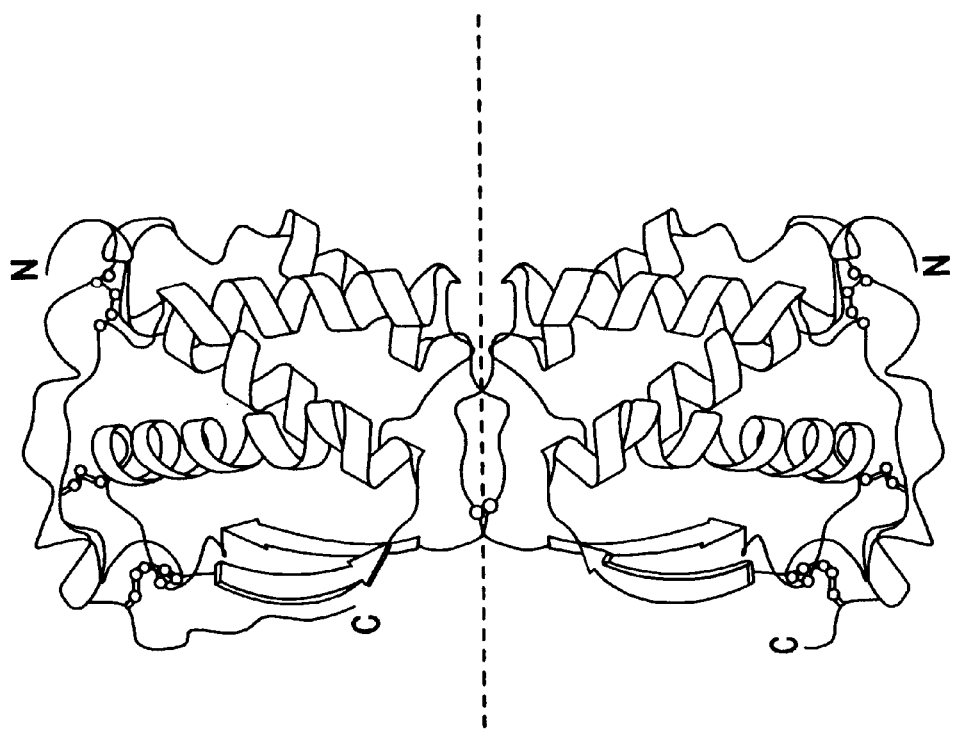

A striking difference from other cytokines and other four helix bundle structures is that the truncated M-CSFα forms a disulfide-linked dimer, in which the bundles are linked end-to-end, forming an extremely flat, elongated structure (approximate dimensions 85×35×25 Å) as shown in FIGS. 3 and 4A and 4B. There are three intramolecular disulfide bonds in each monomer (Cys7-Cys90, Cys8-Cys139, Cys102-Cys146) all of which are at the distal end of the molecule. One interchain disulfide bond (Cys31—Cys31) is located at the dimer interface with the noncrystallographic two-fold symmetry axis passing through it as shown in FIGS. 3 and 4. Mutation experiments indicate that all of the cysteine residues in this form of M-CSF may be necessary for full biological activity. The structure described herein suggests that their role is primarily structural rather than being related to receptor recognition.

Appendix 1 provides the three-dimensional structure of the truncated, recombinant M-CSFα dimer as identified by the alpha carbon positions of the amino acid residues in the sequence. The five carboxy terminal amino acids of each polypeptide of the dimer were not included. As will be recognized to those of skill in the art, the information in Appendix 1 is provided in the format used by the Brookhaven Protein Data Bank.

As shown, the molecule has an unusual topology which identifies important regions of M-CSF with regard to M-CSF receptor binding. Specific residues in helices A, C, and D appear to be involved in the specificity of the interaction. Altering solvent accessible residues in these regions by site directed mutagenesis to increase or decrease side-chain interactions with the receptor may be useful to generate M-CSF agonists or antagonists. For example, changing one or more histidines to non-hydrogen-donor amino acids of similar size may create an M-CSF with altered receptor binding ability.

EXAMPLE 8

Preparation of M-CSF Heterodimers
Purification of M-CSF Monomers

*E. coli* harboring the pL-M-CSF vector for NΔ3CΔ158M-CSFα described in U.S. Pat. No. 4,929,700 or NΔ3CΔ221 M-CSFβ C157S, C159S (Kawasaki, et al., in *Colony-Stimulating Factors*, Dexter, T., Garland, J., and Testa, N., eds. [1990]) were grown in 1 liter of minimal salts medium containing glucose and the appropriate antibiotic. Expression of M-CSF was induced by shifting the temperature to 39° C. for 4 hr. following the addition of casamino acids to 2%. The cells were harvested by centrifugation and lysed by sonication in 50 mM Tris (pH 8.5), 10 mM EDTA. The cell debris was recovered by centrifugation, washed with 30% sucrose containing 10 mM EDTA, and a portion of the refractile body paste was solubilized in 8 M urea under reducing conditions. After incubation at 37° C. for 30 min., the solubilized M-CSF was clarified by centrifugation and filtration, and then loaded onto a Bio-Gel TSK-DEAE-5-PW column (7.5×75 mm) (BioRad Laboratories, Richmond, Calif.) equilibrated in 8 M urea in 10 mM Tris (pH 8.5), 5 mM DTT, 0.5 mM EDTA. The monomeric M-CSF was eluted with a 45-min, 0–0.6 M NaCl gradient. The M-CSF peak fractions were pooled and concentrated to 10 mg/ml with a Centricon 10 microconcentrator (Amicon).
Formation and Analysis of Active M-CSF Heterodimers The M-CSF homodimers were refolded by diluting to a protein concentration of 0.5 mg/ml in precooled 50 mM Tris (H 8.5), 5 mM EDTA, 2 mM reduced glutathione and 1 mM oxidized glutathione, and then incubating at 4° C. The heterodimer was refolded by diluting 158 and 221F monomer pools to 1 mg/ml in the same buffer. To monitor the refolding, size exclusion high pressure liquid chromatography (SE-HPLC) analysis was performed by immediately injecting reaction samples onto a G3000SW Ultropack (Pharmacia LKB Biotechnology, Inc., Piscataway, N.J.) column size-exclusion (7.5×600 mm) equilibrated in PBS (pH 6.8).

Fractionated products were analyzed on reducing SDS-PAGE and stained with Coomassie, according to the method of Laemmli, *Nature* (Canada) 227:680–685 (1970). Biological activity was determined using the M-CSF dependent NFS-60 bioassay (See Example 10 below). Antibody neutralization experiments were carried out by pre-incubating approximately 5,000 units of M-CSF dimer with varying dilutions of the neutralizing M-CSF 5H410 Mab (made to refolded *E. coli* CΔ150 M-CSFα dimer) prior to bioassay. (Halenbeck et al, *Bio/Technology* 7:710 (1989)

The heterodimeric M-CSF product was designed to consist of one chain of short clone (from amino acid 4 to 158) and one chain of long clone (from amino acid 4 to 221). The long-clone chain (221F) also contained substitutions of serine for the two non-essential cysteines (at 157 and 159) to minimize the possibility of higher-order oligomer formation.

Solubilized refractile bodies of M-CSF 158 and 221F were separately chromatographed by DEAE-HPLC in 8 M urea. Only one major protein peak eluted in each case, and the peak fractions were pooled, based on an analysis of purity by non-reducing SDS-PAGE and Coomassie staining (data not shown). The resulting monomer was over 90% pure in each case. The monomers were separately concentrated to 10 mg/ml, diluted in refolding buffer, and refolded at 4° C.

To compare the rates of dimerization of shorn- and long-clone M-CSF, 20 μl of each refolding reaction was injected on a SE-HPLC column at 0, 2. 18 and 72 hr. The amount of dimeric M-CSF formed was determined from the peak area at the molecular weight expected for dimer. In both refolding reactions the M-CSF was mostly equilibrated to monomer at t=0 and had become about 40% dimeric by 2 hr and nearly 75% dimeric by 18 hr. The similarity of the ratio of dimer to monomer between the refolded 158 and 221F strongly suggests that the rate of dimer formation is the same for long- and short-clone M-CSF. Thus, when equal moles of 158 and 221F are present in a refolding reaction, the final relative ratios of 158 homodimer to 221F homodimer to 158/221F heterodimer are predicted to be 1:1:2 (Similar distributions have been observed in vivo for isozymes of lactate dehydrogenase.)

Biological Activity of Refolded Homodimers and Heterodimers

Figure 5A:
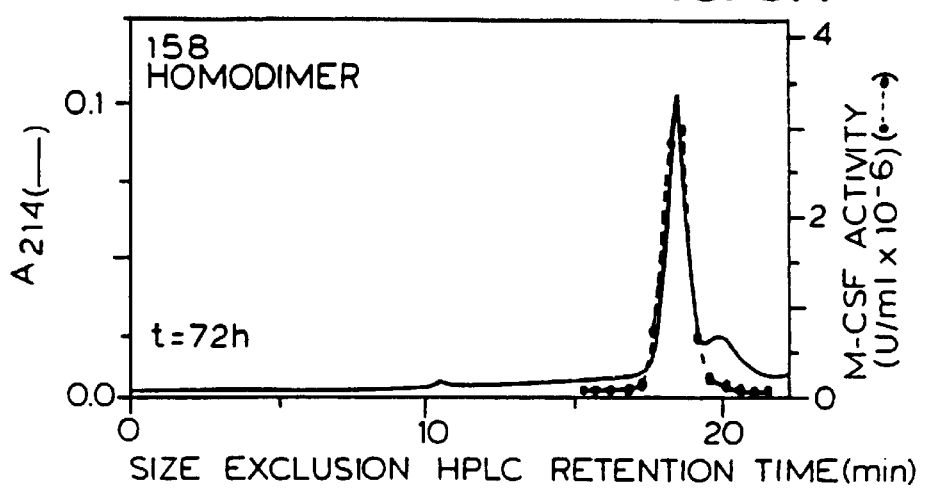
Figure 5B:
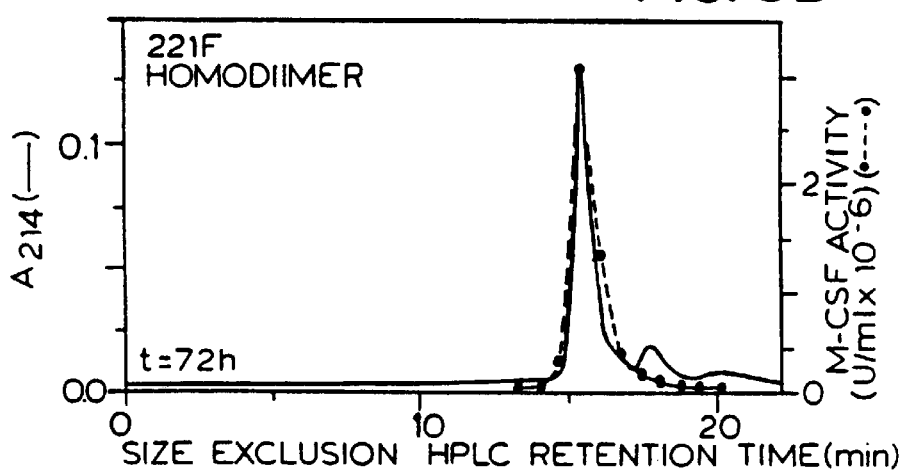
Figure 5C:
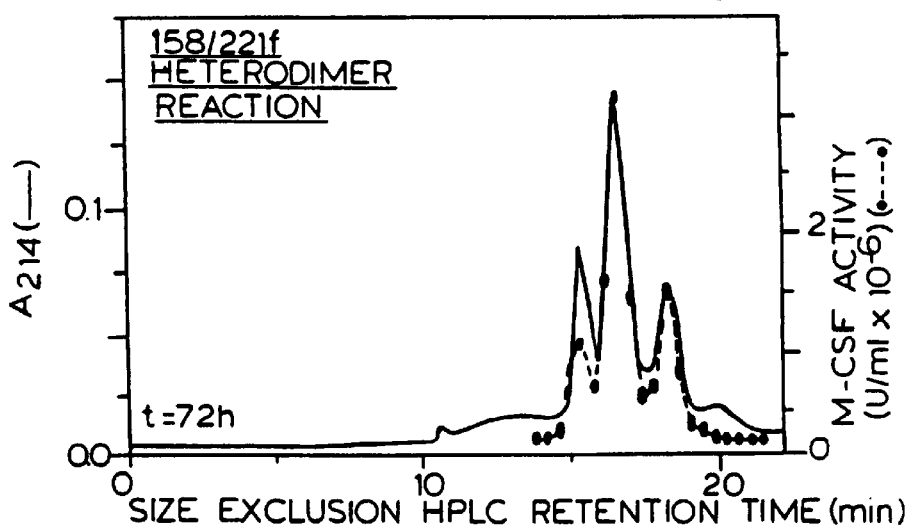

The biological activity of the refolded homodimers and heterodimers described above, was examined using the in vitro M-CSF-dependent NFS-60 bioassay (See Example 10 below). FIGS. 5A–5C show the result of these studies. These SE-HPLC and biological activity profiles analyzed after 72 hr of refolding, show that the heterodimer, FIG. 5C, displays activity very similar to that of the two homodimers, (FIGS. 5A and 5B). Given that the separation of the heterodimer from the homodimers was nearly complete, it can be concluded that the heterodimer is fully biologically active in vitro.

To verify that the M-CSF protein eluting from these columns at the predicted heterodimeric position (between the two homodimers) actually did consist of equal moles of short- and long-clone monomers, analysis of a preparative purification of the 158/221F heterodimer was carried out. Phenyl-HPLC was performed as described above and was shown to completely resolve the heterodimer from the 158 and 221F homodimers, as seen in FIG. 6A.

Preparative Purification of M-CSF Heterodimers

The refolded M-CSF was adjusted to pH 7.0 with 1 N HCl, and ammonium sulfate was added to 1.2 M. The protein was loaded onto a Bio-Gel TSK-Phenyl-5-PW column (7.5×75 mm) (BioRad, Richmond, Calif.) equilibrated in 1.2 M ammonium sulfate, 100 mM phosphate (pH 7.0). The M-CSF was eluted with a decreasing gradient of ammonium sulfate from 40% to 80% buffer B (10 mM phosphate, pH 7.0) in 24 min.

Reducing and non-reducing SDS-PAGE (FIGS. 6B and C) showed that internal controls (the 158 and 221F dimers) were purified to approximately 95% homogeneity by this column, and each consisted of the single expected monomeric band. The gel analysis also showed that the heterodimer was purified to approximately 95% homogeneity and that it consisted of equivalent amounts of 158 and 221F monomers. Recovery of purified 158/221F heterodimer from refractile body paste to final product, was greater than 15%.

The bioactivity of the dimeric M-CSF species was determined and, when compared to the $A_{280}$ profile in FIG. 6A, confirms the finding that the heterodimer is fully active. The specific activity of the 158/221F heterodimer, calculated using the peak fraction, was $8.0 \times 10^7$ units/mg, compared to $9.0 \times 10^7$ and $6.8 \times 10^7$ units/mg for 158 and 221F homodimers, respectively.

The biological activity of all three dimer species was neutralized to the same extent in serial dilution neutralization experiments using the 5H410 M-CSF Mab in the NFS-60 bioassay. This antibody also neutralizes "naturally refolded" Chinese hamster ovary cell (CHO)-expressed M-CSF in a similar fashion. This result further suggests that the refolded conformation of the new M-CSF heterodimer is essentially native-like, at least with regard to the region within the first 150 amino acids that is responsible for in vitro activity.

EXAMPLE 9

Selection of Amino Acid Substitutions in M-CSF Based on Crystallographic Data

The X-ray crystallographic data described above provided sufficient structural information regarding M-CSF to be able to identify a limited subset of the amino acids in the protein that are likely to be crucial for M-CSF receptor binding and biological activity and thus which represented likely candidates for mutagenesis with the ultimate goal of providing M-CSF muteins having altered biological activity (i.e., agonists or antagonists). Based on this information, several criteria were used to generate a list of possible target amino acids for substitution.

The first criterion was solvent exposure or solvent accessibility, which refers to amino acids residues at the surface of the protein. Residues having a solvent accessible surface area of greater than about 0.25 and preferably greater than about 0.4 are preferred based on normalization of the surface area of the amino acid accessible when in the trypeptide gly-x-gly (Kabsch, W. et al., *Biopolymers* 22:2577 (1983)). Residues were chosen which do not interact with other parts of the protein such as the dimer interface in order to maintain the relative orientation of monomers and to avoid disturbing the process of protein folding. Still another criterion used in certain instances in selecting candidate amino acid substitutions is the relationship of the residues to corresponding residues in mouse M-CSF. Another important selection criterion was that the substitutions be non-conservative so as to attempt to disrupt possible hydrogen bonding or hydrophobic interactions with M-CSF receptor residues.

Table 1 lists exemplary amino acid residues and exemplary substitutions. Using the criteria for selecting candidates for substitutions set forth above, those of ordinary skill in the art may readily ascertain other possible candidates for substitution.

TABLE I

Candidate Substitutions

| Wild Type Amino Acid and Location | Substitutions |
|---|---|
| His (H) 15 | Ala (A) or Leu (L) |
| Gln (Q) 17 | Ala (A) or Glu (E) |
| Gln (Q) 79 | Ala (A) or Asp (D) |
| Arg (R) 86 | Glu (E) or Asp (D) |
| Glu (E) 115 | Ala (A) |
| Glu (E) 41 | Lys (K) or Arg (R) |
| Lys (K) 93 | Ala (A) or Glu (E) |
| Asp (D) 99 | Lys (K) or Arg (R) |
| Leu (L) 55 | Gln (Q) or Asp (N) |
| Ser (S) 18 | Ala (A) or Lys (K) |
| Gln (Q) 20 | Ala (A) or Asp (D) |
| Arg (R) 21 | Ala (A), Glu (E), or Asp (D) |
| Ile (I) 75 | Lys (K) or Glu (E) |
| Val (V) 78 | Lys (K) or Arg (R) |
| Leu (L) 85 | Glu (E) or Asn (N) |
| Asp (D) 69 | Lys (K) or Arg (R) |
| Asn (N) 70 | Ala (A) or Glu (E) |
| His (H) 9 | Ala (A) or Asp (D) |
| Asn (N) 63 | Lys (K) or Arg (R) |
| Thr (T) 34 | Gln (Q) or Lys (K) |

It is not expected that every candidate substitution listed will result in the production of M-CSF agonists or antagonists (see Example 12 below). Rather they represent a non-exclusive list of candidates likely to result in the production of agonists or antagonists based on the selection criteria set forth above. It should also be noted that even if a variant does not act as an agonist or antagonist when compared with native M-CSF, the variant is still useful for conventional uses of the ligand (if it retains the same activity as the ligand) or as for example, a diagnostic reagent.

EXAMPLE 10

Preparation of H9A, H15A M-CSF Muteins

A variety of M-CSF muteins with altered solvent-accessible residues from regions of the M-CSF mature N terminus and helices A, C, and D were constructed using techniques known in the art. For example, two histidines in the N-terminal/A helix region were changed to alanine through site-directed mutagenesis of a truncated form of M-CSFα (encoded by pLCSF158A). Involvement of one of three M-CSF histidine residues in M-CSF receptor interaction was implicated by our observation that diethylpyrocarbonate (DEPC) modification of histidines in M-CSF at a 1:100 DEPC:histidine ratio (as described in *Meth. in Enzymol.* 47:431 (1977)) significantly reduced bioactivity.

Plasmid DNA pLCSF158A was prepared from the *E. coli* strain HW22 carrying the plasmid pLCSF158A (U.S. Pat. No. 4,929,700, Example 6, "*E. coli* strain HW22 transformed with pJN653 containing the asp$_{59}$SCSF/NΔ3CΔ158 gene") The strain was grown in 350 ml R2 media (2× Luria Broth containing 1% sodium chloride and no glucose, *J. Bact.*, 74:461 (1957)) containing 50 micrograms/ml ampicillin at 30° C. with shaking overnight. Plasmid DNA was prepared from the cells using a Qiagen-tip 100 column according to the manufacturer's directions.

Twenty micrograms of pLCSF158A DNA were digested with 66 units of HindIII and 66 units of StuI at 37° C. for 3 hr. 20 min. in 200 microliters 1× New England Biolabs NEBuffer 2 (New England Biolabs, Beverly, Mass.). The DNA was extracted with phenol and chloroform, then ethanol precipitated. The DNA was treated with one unit of Calf Intestinal Alkaline Phosphatase in 100 microliters of 1× Dephosphorylation Buffer, supplied by Boehringer Mannheim (Indianapolis, Ind.), at 37° C. for 30 min. An additional unit of Calf Intestinal Alkaline Phosphatase was added to the reaction and incubation was continued at 50° C. for 1 hr.

The resulting DNA was then run on a 1% FMC Bioproducts (Rockland, Me.) Sea KEM® GTG® agarose gel. The 5.7 kb pLCSF158A fragment was cut from the gel and purified on Qiagen (Chatsworth, Calif.) Qiaex beads according to the manufacturer's directions.

Polymerase chain reaction (PCR) was then performed and a PCR product was produced mat contained a mutagenized M-CSF sequence in which histidines 9 and 15 (counting from the mature N-terminus) were altered to alanine (generating an H9A, H15A PCR fragment). The 5' portion of the M-CSF gene was amplified from the plasmid pLCSF158A in a PCR reaction using the primers LF73 and LF74. Details of PCR are provided by Mullis, K. et al., U.S. Pat. No. 4,683,202; Ehrlich, H., U.S. Pat. No. 4,582,788; Saiki et al., U.S. Pat. No. 4,683,195; Mullis, K. B., *Cold Spring Harbor Symp. Quant. Biol.* 51:263–273 (1986); Saiki et al., *Bio/Technology* 3:1008–10012 (1985); and Mullis, K. B. et al., *Meth. Enzymol* 155:335–350 (1987), all of which are incorporated herein by reference. The sequences of these primers are:

LF73

5'-AGGTGTCTCATAGAAAGTTCGGACGCAG-
    GCCTTGTCATGCTCTTCATAATCCTTGG-3' (SEQ ID NO. 1)

LF74

5'-CAGGAGAAAGCTTATGTCTGAATATTGTAGCGCCATGAT-
    TGGGAGTGGAGCCCTGCAG-3'      (SEQ D NO. 2)

The expected PCR product was designed to include 337 bp of pLCSF158A sequence, with the HindIII and StuI sites located at each end of the product for cloning, and the histidine codons for His 9 and His 15, CAC, mutated to an alanine codons, GCC.

This product was amplified in four separate PCR reactions each containing 100 ng of pLCSF158A DNA, 50 pmoles LF73, 50 pmoles LF74, 37.5 μM dNTPS, 5% glycerol, 1× Perkin Elmer Cetus PCR Buffer, and 2.5 units of Perkin Elmer Cetus AmpliTaq® DNA Polymerase in a 100 microliter volume. The amplification was carried out in a Perkin Elmer Cetus DNA thermocycler. Before adding the AmpliTaq®, the reactions were brought to 95° C. The amplification was carried out for 25 cycles ramping to a denaturation temperature of 95° C. in 1 sec., denaturing at 95° C. for 1 min.; ramping to an annealing temperature of 68° C. in 1 sec., annealing at 68° C. 1 min.; ramping to an extension temperature of 72° C. in 30 sec., extending at 72° C. 1 min., 30 sec. Final extension was carried out at 72° C. for 10 min.

Five microliters of each reaction were run on a 3% agarose gel (1.5% FMC Bioproducts SeaKem® GTG® agarose, 1.5% FMC Bioproducts NuSeive® GTG® agarose in Tris-Borate buffer) (FMC Bioproducts, Rockland, Me.). Gels were then stained with ethidium bromide. For each reaction, a major band was visible at approximately 337 bp.

The four reactions were pooled, extracted with phenol and chloroform, precipitated with ethanol, resuspended and digested with 250 units of StuI in a final volume of 500 microliters 1× NEBuffer 2 at 37° C. for 2 hr., 500 units of HindIII were added to the reaction, the volume increased to 1 ml in 1× NEBuffer 2 and digestion was continued at 37° C. for an additional 2.5 hr. The DNA was electrophoresed on a 3% agarose gel. The 300 bp digested product was cut from the gel and purified on Qiagen Qiaex beads according to the manufacturer's directions.

Approximately 68 ng of the HindIII/StuI digested PCR product was then ligated to approximately 28 ng of the 5.7 kb HindIII/StuI digested pLCSF158A vector DNA at an insert-to-vector ratio of approximately 5:1. Ligation was carried out with 1 unit of Boehringer Mannheim T4 DNA ligase in 1× ligation buffer, supplied by the manufacturer, in a 20-microliter volume at 16° C. overnight. As a control 28 ng of the 5.7 kb HindIII/StuI digested pLCSF158A vector DNA was ligated to itself under the same conditions with no insert present.

Half of each ligation mixture was used to transform competent *E. coli* DG116 (ATCC#53606) cells using a protocol similar to the calcium chloride. procedure described in Molecular Cloning a Laboratory Manual Maniatis et al., Cold Spring Harbor Laboratory (1982). Transformed cells were allowed to express at 30° C. with no selection for 90 min., plated on R2-4 (10 g tryptone, 5 g yeast extract, 5 g NaCl, 2 drops antifoam A, 4 ml 50% glucose and 15 g agar in 1 liter) plates containing 50 micrograms/ml ampicillin. The plates were incubated at room temperature 72 hr. One fourth of each transformation was plated. For the ligation containing the insert, 66 ampicillin resistant colonies appeared on the plates. For the ligation with no insert, no colonies appeared.

One of these colonies, designated strain TAF172-2, was picked and cultured in 350 ml R2 broth with 50 micrograms/ml ampicillin at 30° C. with shaking overnight. A frozen stock in 40% glycerol was made from this culture and stored at −70° C. DNA was isolated from the culture using Qiagen-tip 100 columns as described above.

The purified DNA, pTAF172-2, was sequenced using the di-deoxy method and shown to contain the sequence of pLCSF158A coding for M-CSF NΔ3CΔ158 with His 9 and His 15 mutated to encode Ala.

The M-CSF mutein NΔ3CΔ158 H9A, H15A encoded by pTAF172-2 was expressed, purified, refolded to form dimeric protein and assayed essentially as described in U.S. Pat. No. 4,929,700 Example 5, using 8M urea as a denaturant and in the DEAE purification step.

The N-terminal sequence of the purified mutein was determined through 20 cycles, using a standard automated Edman degradation method, and shown to be identical to that of the parental NΔ3CΔ158 M-CSFα reference protein except that His 9 and His 15 had been altered to Ala. Protein concentration was determined using A280 and an extinction co-efficient of 0.68.

The purified mutein dimers were subjected to bioassay using NFS-60 cells which is an M-CSF dependent cell line which forms colonies in the presence of active M-CSF. Standards and purified mutein samples were serially diluted 1:2 in RPMI media (10% fetal bovine serum) in a 50 microliter volume in 96-well microtiter plates. 50 microliters NFS-60 cells (ATCC NO. CRL 1838), maintained in 4000 U/ml M-CSF, washed 2×, and diluted to a concentration of 1×10$^5$ cell/ml, were added to each sample well. Plates were incubated at 37° C., 5% $CO_2$ for 44 h. 5 mg/ml MTT dye was added to each sample and incubation continued for 4h. 20% SDS was added to each sample. The plates were wrapped in foil and left overnight. The absorbance of each sample was read at 570 nm and compared to a standard of known M-CSF concentration. The H9A, H15A mutein showed a specific activity of 7.6×10$^3$ U/mg compared to 6.9×10$^7$ U/mg for the parental M-CSF NΔ3CΔ158 reference in the same assay. This represents a nearly 10,000 fold reduction in biological activity for the mutein. The same M-CSF mutein preparation was shown to have greatly decreased M-CSF receptor-binding ability using the NFS-60 receptor competition assay described in this example. Because the H9A, H15A M-CSF mutein was otherwise not significantly different from the parental M-CSFα, including crystallizability and space group (see Example 12) we believe the decrease in, biological activity is not due to gross deformation of structure but reflects an alteration in important M-CSF receptor contacts.

Using essentially the same methodology, two M-CSF muteins contacting singly substituted histidines at residues 9 and 15 were generated (e.g. H9AL and H15A). The H9A construct utilized LF80:

5'-CAGGAGAAAGCTTATGTCTGAATATTGTAGCGCCATGAT-TGGGAGTGGACACCTGCAG-3'  (SEQ ID NO 3);

and LF73 (described in this example) as the PCR primers. The H15A construct utilized LP81:

5'-CAGGAGAAAGCTTATGTCTGAATATTGTAGCCACATGAT-TGGGAGTGGAGCCCTGCAG-3'  (SEQ ID NO. 4);

and LF 73 (described in this example) as PCR primers. Biological assay of the purified muteins immediately following the refolding step described above showed approximate biological specific activities as follows: 4×10$^6$ U/mg for H9A and less than 3×10$^3$ U/mg for H15A, in an assay which the parental ML-CSF construct displayed 8×10$^7$ U/mg. This information, combined with that described above, suggests that H15A as well as possible H9A represents contacts that are important for M-CSF receptor binding. Nearby solvent accessible residues such as Y6 and S13 (see also Table 1) may also represent M-CSF receptor contact residues. Non-proteinaceous mimics of the side chains of H9, H15, and nearby solvent accessible side chains may represent M-CSF agonists or antagonists. Such residues should be left unchanged in M-CSF mutein constructs designed to retain full M-CSF receptor binding but to have M-CSF antagonist properties because they lack significant M-CSF bioactivity. Homodimers of muteins that retain full receptor-binding ability and display significantly reduced bioactivity should represent M-CSF antagonists. M-CSF muteins that are greatly decreased in both M-CSF bioactivity and receptor binding ability (such as H15A) may generally be useful in M-CSF immunoassay applications and might represent useful therapeutic agents for patients having auto-antibodies to M-CSF.

EXAMPLE 11

Preparation of Q20A, V78K M-CSF Muteins

Using essentially the same methodology described in Example 10, a double mutant of M-CSF (Q20A, V78K) was constructed to test the importance of solvent accessible residues in the central portion of helices A and C. The followings PCR primers were used.

LF63

5'-AGGAGAAAGCTTATGTCTGAATATTG-
TAGCCACATGATTGGGAGTGGACACCTGCAGT CTCTG-
GCTCGGCTG-3' (SEQ ED NO. 5)

LF64

5'-GGACGCAGGCCTTTGTCATGCTCTTCAT-
AATCCTTGGTGAAGCAGCTCTTCAGCCTCAA
AGAGAGTTCCTGCAGCTGTTTAATGGC-3' (SEQ ID NO. 6)

The resulting mutein was expressed, refolded, purified, and assayed as described in Example 8. The specific biological activity was $1.4 \times 10^7$ U/mg, approximately 8–10 fold lower than that of the parental M-CSFα reference standard. The receptor binding activity of this mutein was also decreased.

This result again supports the prediction of over crystallographic study of truncated M-CSFα which concluded that important M-CSF receptor contact residues exist among the solvent accessible residues in helices A and/or C and/or D. Certain of these mutations will, as we have shown, have lower biological activity and lower M-CSF receptor-binding ability. Some may have lower biological activity without a decrease in receptor-binding ability. Some may have increased biologicals activity and receptor binding ability, and some may have no affect on either.

Two examples of the latter are Q17A, R21A (produced using PCR primers LF72:

5'-TTGTAGCCACATGATTGGGAGTGGACAC-
CTGGCGTCTCTGCAGGCGCTGATTGAC-3' and
LF73 (described in Example 9) and E115A, N119A (produced using LF75:

5'-CATGACAAGGCCTGCGTCCGAACMCTAT-
GAGACACCTTCCCAGTTGCTGGCGAAGC TCAAGGCT-
GTCTTMAATG-3' (SEQ ID NO. 7);

and
LF79

5'-GGATCAGGATCCCTCGGACTGCCTCTC-3'(SEQ ID NO. 8)).

Both of these constructs changed side chain properties of solvent-accessible amino) acids in the areas of interest but did not affect biological specific activity, compared to the parental reference molecule. These results indicate that residues Q17, R21, E115, and N119 do not need to be altered in muteins designed to have M-CSF agonist or antagonist activity. In fact, to minimize the likelihood of antibody formation to potentially administered M-CSF-based proteinaceous drugs, it is desirable to retain the solvent-accessible parental M-CSF residues (to resemble the native molecule) whenever possible.

The retained activity of the muteins including changes at Q17, R21, E115, and N119 does not rule out large affects on activity contributed by nearby residues (such as H15). In fact, the regions we have altered are predicted by the crystal structure to be important for receptor binding and/or signaling. Antagonistic M-CSF muteins may require use of multiple residue changes per mutein or use of heterodimeric molecules containing one or more mutations in each polypeptide chain, since M-CSF residues important in receptor signaling are believed to be composed of discontinuous regions of M-CSF.

EXAMPLE 12

Formation of M-CSF Heterodimers Having Decreased Receptor-Binding Ability and/or Decreased Biological Specific Activity M-CSF can be folded in vitro to generate fully active heterodimers, as shown in Example 8. By making heterodimers of M-CSF which incorporate M-CSF muteins with altered M-CSF signaling ability, it should be possible to generate antagonists of M-CSF useful for treatment of patients with M-CSF mediated diseases. To generate a heterodimer containing one subunit of M-CSFα NΔ3CΔ158 H9A, H15A and one subunit of M-CSFβ NΔ3CΔ221 C157S, C159S, each mutein was expressed in E. coli and purified separately by DEAE Sepharose under denaturing and reducing conditions as described in Example 8. The two muteins subunits were mixed together prior to refolding to generate a solution containing a final mutein molar ratio of 1:1, then this solution was diluted to 0.2 mg/ml with refolding buffer as described in Example 8. Following refolding, the heterodimeric molecule was separated from the homodimers by two consecutive passes over a Phenyl TSK-5-PW HPLC column as described in Example 8. No contaminants were detected when the purified heterodimer preparation was examined by non-reduced SDS-PAGE or size exclusion HPLC using a BioSil SEC250 column (BioRad).

The purified heterodimer was submitted to the NFS60 cell based bioassay described in Example 8. The calculated specific activity was $2.9 \times 10^6$ U/mg which correlated to a 35-fold reduction as compared to the activity of the parental M-CSF heterodimer described in Example 10. The relative binding affinity to cell surface M-CSF receptor was measured by radioligand displacement in which the displacement of $^{125}$I-M-CSF from an M-CSF receptor by an M-CSF mutein was measured using methods well known in the art. In brief, the following were added in a final volume of 100 µl in each well of a 96-well cell culture plate: approximately 80,000 cpm of purified recombinant human M-CSF labeled with $^{125}$I (using Iodobeads as described by the manufacturer, Pierce, Rockford, Ill.), 300,000 NFS-60 cells that had been washed and then grown for 18 hours in growth medium minus the normal maintenance level of M-CSF, plus unlabeled M-CSF that had been serially diluted in the same medium. The plates were incubated at 4° C. for 20 hours and the cells were collected on glass-fiber filters. Maximum binding was measured in the absence of unlabeled M-CSF and non-specific binding was measured in the presence of 1000-fold greater concentration of unlabeled M-CSF (compared to labeled M-CSF). The concentration of M-CSF required to inhibit 50% of the labeled M-CSF binding to the cells ($IC_{50}$) was used to determine differences in affinity. Results are expressed as percent displacement of radioactive M-CSF versus mutein concentration (FIG. 7). The $IC_{50}$ of the heterodimer (FIG. 7 closed squares) was reduced 30-fold to about 500 pM as compared to an $IC_{50}$ of about 17 pM for M-CSFα NΔ3CΔ158 (158) (FIG. 7 closed circles). The similarity between the reduction in specific activity and receptor affinity of the heterodimer indicates that the reduction in bioactivity was due to decreased receptor-binding ability. Similarly, the binding affinities of the Q20A, V78KF (FIG. 7 open circles) and −H9A, H15A (open squares) muteins were also measured in this radioligand displacement assay. The Q20A, V78K mutein had an $IC_{50}$ of about 100 pM and the −H9A, H15A mutein has an $IC_{50}$ of about 1 µM, correlating to decreased binding affinities of 5-fold and 50,000-fold, respectively. For each mutein, the reduction in receptor affinity was similar to the reduction in specific activity, again indicating that the reduction in bioactivity was due to reduced receptor-binding ability.

EXAMPLE 13

Crystallization and Characterization Of M-CSF H9A, H15A Muteins

The H9A, H15A mutein described in Example 10 was crystallized using the hanging drop method described in Examples 1 and 2 using the following buffer conditions: 30% polyethylene glycol 4000; 100 mM $Li_2SO_4$; and 100 mM Tris pH 8.5. The crystals produced under these conditions were rhombohedral prisms having dimensions of 0.7 mm×0.2 mm×0.2 mm. X-ray crystallographic analysis using precession photographs showed crystals in the $P2_12_12_1$ space group with cell dimensions of a=33.99, b=65.37, c=159.90, d=90, e=90, and f=90 angstroms and diffract to a nominal resolution of 3 angstroms. These physical properties are essentially the same as those observed for the parental NΔ3CΔ158 M-CSFα molecule and suggests that the biological effects of the H9A, H15A alterations are not the consequence of gross global alterations in M-CSF structure, but rather are the result of altered side chains that are important in interacting with the M-CSF receptor. Alteration of those histidine side chains may have affected receptor binding by changing atoms that interact with, stabilize or facilitate receptor binding or changes in receptor conformation. Changes such as H15A may also have affected these functions by altering the position of the nearby side chain in M-CSF, most likely in the A and/or C helix regions.

The foregoing examples are presented by way of example and are not intended to limit the scope of the invention as set forth in the appended claims.

APPENDIX 1

| ATOM | 10  | CA | SER | 4  | 63.753 | 80.590  | 222.385 | 1.00 | 58.89 |
|------|-----|----|-----|-----|--------|---------|---------|------|-------|
| ATOM | 13  | CA | GLU | 5  | 64.883 | 77.664  | 219.972 | 1.00 | 59.56 |
| ATOM | 23  | CA | TYR | 6  | 62.285 | 76.840  | 217.324 | 1.00 | 54.54 |
| ATOM | 37  | CA | CYS | 7  | 63.509 | 80.109  | 215.834 | 1.00 | 54.96 |
| ATOM | 44  | CA | SER | 8  | 66.853 | 79.529  | 214.160 | 1.00 | 54.41 |
| ATOM | 52  | CA | HIS | 9  | 65.466 | 77.798  | 211.053 | 1.00 | 55.11 |
| ATOM | 65  | CA | MET | 10 | 61.857 | 78.767  | 211.073 | 1.00 | 50.66 |
| ATOM | 74  | CA | ILE | 11 | 62.173 | 80.905  | 207.970 | 1.00 | 48.31 |
| ATOM | 83  | CA | GLY | 12 | 63.487 | 78.618  | 205.354 | 1.00 | 52.83 |
| ATOM | 88  | CA | SER | 13 | 64.609 | 79.967  | 201.952 | 1.00 | 53.13 |
| ATOM | 96  | CA | GLY | 14 | 61.665 | 78.009  | 200.514 | 1.00 | 46.05 |
| ATOM | 101 | CA | HIS | 15 | 59.455 | 80.924  | 201.933 | 1.00 | 40.25 |
| ATOM | 114 | CA | LEU | 16 | 62.210 | 83.200  | 200.992 | 1.00 | 41.58 |
| ATOM | 123 | CA | GLN | 17 | 62.153 | 82.266  | 197.328 | 1.00 | 46.17 |
| ATOM | 135 | CA | SER | 18 | 58.378 | 81.868  | 197.227 | 1.00 | 46.55 |
| ATOM | 143 | CA | LEU | 19 | 58.280 | 85.544  | 198.199 | 1.00 | 44.75 |
| ATOM | 152 | CA | GLN | 20 | 60.814 | 86.044  | 195.458 | 1.00 | 39.32 |
| ATOM | 164 | CA | ARG | 21 | 58.457 | 84.718  | 192.736 | 1.00 | 36.91 |
| ATOM | 181 | CA | LEU | 22 | 55.610 | 86.694  | 194.252 | 1.00 | 38.27 |
| ATOM | 190 | CA | ILE | 23 | 57.676 | 89.822  | 193.465 | 1.00 | 34.84 |
| ATOM | 199 | CA | ASP | 24 | 58.677 | 88.274  | 190.086 | 1.00 | 31.50 |
| ATOM | 208 | CA | SER | 25 | 55.086 | 87.802  | 188.978 | 1.00 | 31.73 |
| ATOM | 216 | CA | GLN | 26 | 54.284 | 91.540  | 189.154 | 1.00 | 33.24 |
| ATOM | 228 | CA | MET | 27 | 53.961 | 93.634  | 186.082 | 1.00 | 34.82 |
| ATOM | 237 | CA | GLU | 28 | 56.227 | 96.566  | 186.089 | 1.00 | 36.54 |
| ATOM | 247 | CA | THR | 29 | 53.758 | 99.303  | 186.920 | 1.00 | 44.80 |
| ATOM | 256 | CA | SER | 30 | 54.590 | 102.747 | 188.323 | 1.00 | 49.40 |
| ATOM | 264 | CA | CYS | 31 | 51.427 | 103.423 | 190.046 | 1.00 | 43.03 |
| ATOM | 271 | CA | GLN | 32 | 52.166 | 104.336 | 193.613 | 1.00 | 33.74 |
| ATOM | 283 | CA | ILE | 33 | 50.430 | 102.961 | 196.634 | 1.00 | 32.48 |
| ATOM | 292 | CA | THR | 34 | 50.240 | 104.213 | 200.133 | 1.00 | 38.94 |
| ATOM | 301 | CA | PHE | 35 | 51.291 | 102.173 | 203.199 | 1.00 | 39.16 |
| ATOM | 313 | CA | GLU | 36 | 52.707 | 102.849 | 206.761 | 1.00 | 32.09 |
| ATOM | 323 | CA | PHE | 37 | 56.073 | 101.358 | 207.299 | 1.00 | 25.78 |
| ATOM | 335 | CA | VAL | 38 | 59.082 | 101.751 | 209.490 | 1.00 | 34.46 |
| ATOM | 343 | CA | ASP | 39 | 61.044 | 104.798 | 208.714 | 1.00 | 44.03 |
| ATOM | 352 | CA | GLN | 40 | 64.648 | 103.690 | 208.314 | 1.00 | 54.20 |
| ATOM | 364 | CA | GLU | 41 | 65.924 | 107.142 | 209.332 | 1.00 | 52.01 |
| ATOM | 374 | CA | GLN | 42 | 63.934 | 107.629 | 212.631 | 1.00 | 44.26 |
| ATOM | 386 | CA | LEU | 43 | 64.770 | 104.161 | 213.955 | 1.00 | 45.54 |
| ATOM | 395 | CA | ALA | 44 | 68.126 | 102.952 | 212.789 | 1.00 | 51.53 |
| ATOM | 401 | CA | ASP | 45 | 69.175 | 100.197 | 215.232 | 1.00 | 47.92 |
| ATOM | 410 | CA | PRO | 46 | 68.861 | 97.054  | 213.098 | 1.00 | 45.27 |
| ATOM | 417 | CA | VAL | 47 | 67.352 | 94.587  | 215.613 | 1.00 | 39.92 |
| ATOM | 425 | CA | CYS | 48 | 64.862 | 97.220  | 216.692 | 1.00 | 36.44 |
| ATOM | 432 | CA | TYR | 49 | 64.089 | 98.158  | 213.105 | 1.00 | 37.39 |
| ATOM | 446 | CA | LEU | 50 | 63.436 | 94.474  | 212.189 | 1.00 | 36.15 |
| ATOM | 455 | CA | LYS | 51 | 61.603 | 94.029  | 215.472 | 1.00 | 38.66 |
| ATOM | 468 | CA | LYS | 52 | 59.322 | 96.862  | 214.367 | 1.00 | 41.72 |
| ATOM | 481 | CA | ALA | 53 | 59.229 | 96.177  | 210.534 | 1.00 | 35.81 |
| ATOM | 487 | CA | PHE | 54 | 58.096 | 92.701  | 211.432 | 1.00 | 40.82 |

APPENDIX 1-continued

| ATOM | 499 | CA | LEU | 55 | 55.236 | 93.733 | 213.614 | 1.00 | 42.59 |
|---|---|---|---|---|---|---|---|---|---|
| ATOM | 508 | CA | LEU | 56 | 54.205 | 95.869 | 210.697 | 1.00 | 44.24 |
| ATOM | 517 | CA | VAL | 57 | 54.596 | 93.257 | 207.992 | 1.00 | 35.10 |
| ATOM | 525 | CA | GLN | 58 | 51.646 | 91.431 | 209.628 | 1.00 | 39.91 |
| ATOM | 537 | CA | ASP | 59 | 49.277 | 94.254 | 208.663 | 1.00 | 39.60 |
| ATOM | 546 | CA | ILE | 60 | 50.755 | 94.729 | 205.185 | 1.00 | 37.05 |
| ATOM | 555 | CA | MET | 61 | 50.303 | 90.932 | 204.676 | 1.00 | 33.86 |
| ATOM | 564 | CA | GLU | 62 | 46.766 | 90.931 | 206.028 | 1.00 | 48.10 |
| ATOM | 574 | CA | ASP | 63 | 45.602 | 94.198 | 204.286 | 1.00 | 49.51 |
| ATOM | 583 | CA | THR | 64 | 47.659 | 95.244 | 201.187 | 1.00 | 42.65 |
| ATOM | 592 | CA | MET | 65 | 49.106 | 92.155 | 199.603 | 1.00 | 37.90 |
| ATOM | 601 | CA | ARG | 66 | 45.646 | 91.249 | 198.376 | 1.00 | 39.50 |
| ATOM | 618 | CA | PHE | 67 | 45.516 | 88.245 | 195.824 | 1.00 | 35.13 |
| ATOM | 630 | CA | ARG | 68 | 42.655 | 86.013 | 194.326 | 1.00 | 44.68 |
| ATOM | 647 | CA | ASP | 69 | 41.727 | 83.454 | 196.865 | 1.00 | 47.42 |
| ATOM | 656 | CA | ASN | 70 | 43.117 | 80.057 | 195.984 | 1.00 | 44.47 |
| ATOM | 667 | CA | THR | 71 | 45.873 | 81.088 | 193.518 | 1.00 | 34.80 |
| ATOM | 676 | CA | PRO | 72 | 49.607 | 80.251 | 194.114 | 1.00 | 29.78 |
| ATOM | 683 | CA | ASN | 73 | 50.307 | 83.745 | 195.418 | 1.00 | 28.47 |
| ATOM | 694 | CA | ALA | 74 | 47.469 | 83.922 | 197.953 | 1.00 | 23.24 |
| ATOM | 700 | CA | ILE | 75 | 48.690 | 80.431 | 199.144 | 1.00 | 22.87 |
| ATOM | 709 | CA | ALA | 76 | 52.212 | 81.892 | 199.669 | 1.00 | 29.47 |
| ATOM | 715 | CA | ILE | 77 | 50.816 | 84.796 | 201.668 | 1.00 | 37.21 |
| ATOM | 724 | CA | VAL | 78 | 48.902 | 82.158 | 203.857 | 1.00 | 33.69 |
| ATOM | 732 | CA | GLN | 79 | 52.207 | 80.382 | 204.466 | 1.00 | 33.36 |
| ATOM | 744 | CA | LEU | 80 | 54.040 | 83.518 | 205.449 | 1.00 | 32.55 |
| ATOM | 753 | CA | GLN | 81 | 51.152 | 84.517 | 207.743 | 1.00 | 35.07 |
| ATOM | 765 | CA | GLU | 82 | 51.541 | 81.115 | 209.443 | 1.00 | 37.26 |
| ATOM | 775 | CA | LEU | 83 | 55.367 | 81.348 | 209.619 | 1.00 | 35.10 |
| ATOM | 784 | CA | SER | 84 | 54.960 | 84.840 | 211.066 | 1.00 | 39.64 |
| ATOM | 792 | CA | LEU | 85 | 52.608 | 83.541 | 213.704 | 1.00 | 42.55 |
| ATOM | 801 | CA | ARG | 86 | 54.984 | 80.903 | 215.121 | 1.00 | 42.96 |
| ATOM | 818 | CA | LEU | 87 | 57.916 | 83.317 | 214.670 | 1.00 | 45.11 |
| ATOM | 827 | CA | LYS | 88 | 56.504 | 85.876 | 217.138 | 1.00 | 50.71 |
| ATOM | 840 | CA | SER | 89 | 57.621 | 83.610 | 219.825 | 1.00 | 54.58 |
| ATOM | 848 | CA | CYS | 90 | 61.211 | 84.524 | 219.014 | 1.00 | 46.79 |
| ATOM | 855 | CA | PHE | 91 | 60.235 | 88.070 | 219.743 | 1.00 | 46.37 |
| ATOM | 867 | CA | THR | 92 | 59.619 | 89.812 | 223.026 | 1.00 | 52.01 |
| ATOM | 876 | CA | ALA | 93 | 56.916 | 92.445 | 223.523 | 1.00 | 56.09 |
| ATOM | 882 | CA | ASP | 94 | 57.914 | 96.123 | 223.998 | 1.00 | 59.35 |
| ATOM | 891 | CA | TYR | 95 | 55.685 | 99.100 | 225.194 | 1.00 | 66.22 |
| ATOM | 905 | CA | GLU | 96 | 52.401 | 100.066 | 223.612 | 1.00 | 65.51 |
| ATOM | 915 | CA | GLU | 97 | 53.343 | 103.890 | 223.182 | 1.00 | 62.60 |
| ATOM | 925 | CA | HIS | 98 | 56.046 | 102.712 | 220.836 | 1.00 | 58.47 |
| ATOM | 938 | CA | ASP | 99 | 53.422 | 100.733 | 218.887 | 1.00 | 59.97 |
| ATOM | 947 | CA | LYS | 100 | 52.950 | 103.470 | 216.162 | 1.00 | 57.00 |
| ATOM | 960 | CA | ALA | 101 | 56.259 | 105.270 | 216.975 | 1.00 | 48.82 |
| ATOM | 966 | CA | CYS | 102 | 58.861 | 105.450 | 214.154 | 1.00 | 42.41 |
| ATOM | 973 | CA | VAL | 103 | 56.175 | 104.773 | 211.621 | 1.00 | 33.87 |
| ATOM | 981 | CA | ARG | 104 | 55.993 | 106.851 | 208.456 | 1.00 | 42.76 |
| ATOM | 998 | CA | THR | 105 | 53.577 | 106.853 | 205.501 | 1.00 | 38.00 |
| ATOM | 1007 | CA | PHE | 106 | 54.931 | 105.944 | 202.136 | 1.00 | 33.48 |
| ATOM | 1019 | CA | TYR | 107 | 53.853 | 106.546 | 198.455 | 1.00 | 34.28 |
| ATOM | 1033 | CA | GLU | 108 | 55.765 | 103.906 | 196.543 | 1.00 | 33.88 |
| ATOM | 1043 | CA | THR | 109 | 55.266 | 101.309 | 193.854 | 1.00 | 36.94 |
| ATOM | 1052 | CA | PRO | 110 | 53.745 | 97.857 | 194.657 | 1.00 | 29.84 |
| ATOM | 1059 | CA | LEU | 111 | 57.132 | 96.374 | 193.761 | 1.00 | 35.66 |
| ATOM | 1068 | CA | GLN | 112 | 58.991 | 98.756 | 196.160 | 1.00 | 33.48 |
| ATOM | 1080 | CA | LEU | 113 | 56.612 | 97.691 | 198.912 | 1.00 | 24.26 |
| ATOM | 1089 | CA | LEU | 114 | 57.253 | 93.932 | 198.091 | 1.00 | 30.75 |
| ATOM | 1098 | CA | GLU | 115 | 61.063 | 94.385 | 197.984 | 1.00 | 39.68 |
| ATOM | 1108 | CA | LYS | 116 | 60.805 | 95.824 | 201.526 | 1.00 | 39.24 |
| ATOM | 1121 | CA | VAL | 117 | 58.669 | 92.840 | 202.743 | 1.00 | 32.46 |
| ATOM | 1129 | CA | LYS | 118 | 61.312 | 90.620 | 201.111 | 1.00 | 37.34 |
| ATOM | 1142 | CA | ASN | 119 | 64.231 | 92.316 | 202.959 | 1.00 | 39.46 |
| ATOM | 1153 | CA | VAL | 120 | 62.470 | 92.033 | 206.370 | 1.00 | 32.07 |
| ATOM | 1161 | CA | PHE | 121 | 61.935 | 88.268 | 206.034 | 1.00 | 26.35 |
| ATOM | 1173 | CA | ASN | 122 | 65.404 | 88.049 | 204.416 | 1.00 | 36.04 |
| ATOM | 1184 | CA | GLU | 123 | 67.372 | 89.816 | 207.138 | 1.00 | 40.82 |
| ATOM | 1194 | CA | THR | 124 | 65.331 | 88.435 | 210.122 | 1.00 | 41.72 |
| ATOM | 1203 | CA | LYS | 125 | 66.456 | 85.000 | 208.648 | 1.00 | 43.07 |
| ATOM | 1216 | CA | ASN | 126 | 70.010 | 86.339 | 208.179 | 1.00 | 48.89 |
| ATOM | 1227 | CA | LEU | 127 | 70.000 | 87.300 | 211.903 | 1.00 | 47.97 |
| ATOM | 1236 | CA | LEU | 128 | 68.315 | 84.194 | 213.435 | 1.00 | 47.21 |
| ATOM | 1245 | CA | ASP | 129 | 71.086 | 82.134 | 211.864 | 1.00 | 50.11 |
| ATOM | 1254 | CA | LYS | 130 | 73.448 | 84.146 | 214.117 | 1.00 | 52.04 |
| ATOM | 1267 | CA | ASP | 131 | 71.442 | 84.303 | 217.451 | 1.00 | 49.48 |
| ATOM | 1276 | CA | TRP | 132 | 67.946 | 82.685 | 218.322 | 1.00 | 53.33 |
| ATOM | 1292 | CA | ASN | 133 | 67.568 | 85.178 | 221.086 | 1.00 | 59.61 |

APPENDIX 1-continued

| ATOM | 1303 | CA | ILE | 134 | 68.572 | 88.447 | 219.305 | 1.00 | 49.82 |
|------|------|----|-----|-----|--------|--------|---------|------|-------|
| ATOM | 1312 | CA | PHE | 135 | 64.945 | 89.516 | 219.045 | 1.00 | 54.55 |
| ATOM | 1324 | CA | SER | 136 | 64.745 | 89.689 | 222.796 | 1.00 | 62.26 |
| ATOM | 1332 | CA | LYS | 137 | 66.563 | 93.119 | 222.569 | 1.00 | 54.38 |
| ATOM | 1345 | CA | ASN | 138 | 64.785 | 95.734 | 224.504 | 1.00 | 58.71 |
| ATOM | 1356 | CA | CYS | 139 | 63.902 | 98.337 | 222.050 | 1.00 | 51.21 |
| ATOM | 1363 | CA | ASN | 140 | 61.704 | 100.578 | 224.157 | 1.00 | 50.25 |
| ATOM | 1374 | CA | ASN | 141 | 64.219 | 103.338 | 224.061 | 1.00 | 58.30 |
| ATOM | 1385 | CA | SER | 142 | 65.158 | 102.992 | 220.352 | 1.00 | 52.18 |
| ATOM | 1393 | CA | PHE | 143 | 61.498 | 103.434 | 219.645 | 1.00 | 45.87 |
| ATOM | 1405 | CA | ALA | 144 | 61.829 | 106.488 | 221.831 | 1.00 | 47.49 |
| ATOM | 1411 | CA | GLU | 145 | 64.873 | 108.022 | 220.050 | 1.00 | 49.94 |
| ATOM | 1421 | CA | CYS | 146 | 62.489 | 108.299 | 217.017 | 1.00 | 53.65 |
| ATOM | 1428 | CA | SER | 147 | 60.005 | 111.197 | 217.009 | 1.00 | 57.45 |
| ATOM | 1436 | CA | SER | 148 | 57.163 | 110.805 | 214.395 | 1.00 | 59.53 |
| ATOM | 1444 | CA | ALA | 149 | 54.284 | 108.658 | 214.945 | 1.00 | 59.20 |
| ATOM | 1450 | CA | GLY | 150 | 51.655 | 108.783 | 212.248 | 1.00 | 61.95 |
| ATOM | 1455 | CA | HIS | 151 | 48.764 | 106.945 | 210.680 | 1.00 | 69.20 |
| ATOM | 1468 | CA | GLU | 152 | 46.475 | 107.377 | 207.803 | 1.00 | 76.61 |
| ATOM | 1478 | CA | ALA | 153 | 45.813 | 106.188 | 204.264 | 1.00 | 78.85 |
| ATOM | 1492 | CA | SER | 404 | 43.875 | 81.916 | 155.536 | 1.00 | 38.68 |
| ATOM | 1495 | CA | GLU | 405 | 41.939 | 78.947 | 156.798 | 1.00 | 43.57 |
| ATOM | 1505 | CA | TYR | 406 | 44.549 | 78.204 | 159.422 | 1.00 | 41.97 |
| ATOM | 1519 | CA | CYS | 407 | 43.251 | 81.196 | 161.434 | 1.00 | 36.99 |
| ATOM | 1526 | CA | SER | 408 | 41.011 | 78.917 | 163.442 | 1.00 | 34.02 |
| ATOM | 1534 | CA | HIS | 409 | 43.988 | 77.122 | 165.021 | 1.00 | 40.02 |
| ATOM | 1547 | CA | MET | 410 | 46.155 | 79.994 | 165.895 | 1.00 | 36.48 |
| ATOM | 1556 | CA | ILE | 411 | 44.849 | 80.843 | 169.353 | 1.00 | 37.88 |
| ATOM | 1565 | CA | GLY | 412 | 44.508 | 77.692 | 171.141 | 1.00 | 39.09 |
| ATOM | 1570 | CA | SER | 413 | 43.275 | 77.480 | 174.756 | 1.00 | 45.21 |
| ATOM | 1578 | CA | GLY | 414 | 46.813 | 77.142 | 176.120 | 1.00 | 41.00 |
| ATOM | 1583 | CA | HIS | 415 | 47.238 | 80.801 | 175.208 | 1.00 | 38.01 |
| ATOM | 1596 | CA | LEU | 416 | 44.181 | 81.554 | 177.458 | 1.00 | 39.12 |
| ATOM | 1605 | CA | GLN | 417 | 45.501 | 79.575 | 180.501 | 1.00 | 39.79 |
| ATOM | 1617 | CA | SER | 418 | 48.547 | 81.846 | 180.317 | 1.00 | 36.95 |
| ATOM | 1625 | CA | LEU | 419 | 46.482 | 85.106 | 180.212 | 1.00 | 33.42 |
| ATOM | 1634 | CA | GLN | 420 | 44.564 | 83.708 | 183.162 | 1.00 | 38.37 |
| ATOM | 1646 | CA | ARG | 421 | 47.839 | 82.875 | 185.041 | 1.00 | 41.95 |
| ATOM | 1663 | CA | LEU | 422 | 49.151 | 86.514 | 184.405 | 1.00 | 33.04 |
| ATOM | 1672 | CA | ILE | 423 | 45.854 | 87.864 | 185.738 | 1.00 | 25.14 |
| ATOM | 1681 | CA | ASP | 424 | 45.824 | 85.549 | 188.861 | 1.00 | 32.93 |
| ATOM | 1690 | CA | SER | 425 | 49.394 | 86.494 | 189.904 | 1.00 | 30.92 |
| ATOM | 1698 | CA | GLN | 426 | 48.776 | 90.276 | 189.999 | 1.00 | 29.47 |
| ATOM | 1710 | CA | MET | 427 | 48.379 | 91.899 | 193.372 | 1.00 | 31.04 |
| ATOM | 1719 | CA | GLU | 428 | 44.978 | 93.418 | 193.655 | 1.00 | 42.94 |
| ATOM | 1729 | CA | THR | 429 | 45.965 | 96.999 | 194.423 | 1.00 | 48.52 |
| ATOM | 1738 | CA | SER | 430 | 43.656 | 99.720 | 193.224 | 1.00 | 48.67 |
| ATOM | 1746 | CA | CYS | 431 | 46.604 | 101.354 | 191.803 | 1.00 | 52.34 |
| ATOM | 1753 | CA | GLN | 432 | 45.813 | 102.789 | 188.396 | 1.00 | 50.77 |
| ATOM | 1765 | CA | ILE | 433 | 47.826 | 103.166 | 185.221 | 1.00 | 51.17 |
| ATOM | 1774 | CA | THR | 434 | 46.923 | 105.057 | 182.065 | 1.00 | 52.62 |
| ATOM | 1783 | CA | PHE | 435 | 46.641 | 103.293 | 178.672 | 1.00 | 50.53 |
| ATOM | 1795 | CA | GLU | 436 | 45.167 | 103.968 | 175.164 | 1.00 | 50.56 |
| ATOM | 1805 | CA | PHE | 437 | 42.643 | 101.271 | 174.193 | 1.00 | 46.56 |
| ATOM | 1817 | CA | VAL | 438 | 39.404 | 101.233 | 172.116 | 1.00 | 52.14 |
| ATOM | 1825 | CA | ASP | 439 | 36.342 | 103.107 | 173.476 | 1.00 | 59.69 |
| ATOM | 1834 | CA | GLN | 440 | 33.750 | 100.386 | 173.243 | 1.00 | 63.82 |
| ATOM | 1846 | CA | GLU | 441 | 30.764 | 102.682 | 173.229 | 1.00 | 64.79 |
| ATOM | 1856 | CA | GLN | 442 | 31.810 | 104.569 | 170.091 | 1.00 | 59.01 |
| ATOM | 1868 | CA | LEU | 443 | 32.994 | 101.521 | 168.139 | 1.00 | 55.78 |
| ATOM | 1877 | CA | LYS | 444 | 30.279 | 99.137 | 169.086 | 1.00 | 54.82 |
| ATOM | 1890 | CA | ASP | 445 | 30.862 | 96.668 | 166.093 | 1.00 | 51.31 |
| ATOM | 1899 | CA | PRO | 446 | 32.144 | 93.267 | 167.135 | 1.00 | 47.34 |
| ATOM | 1906 | CA | VAL | 447 | 34.363 | 92.592 | 164.111 | 1.00 | 41.42 |
| ATOM | 1914 | CA | CYS | 448 | 35.680 | 96.184 | 163.845 | 1.00 | 39.44 |
| ATOM | 1921 | CA | TYR | 449 | 36.273 | 96.949 | 167.607 | 1.00 | 40.33 |
| ATOM | 1935 | CA | LEU | 450 | 38.224 | 93.580 | 167.624 | 1.00 | 30.87 |
| ATOM | 1944 | CA | LYS | 451 | 39.989 | 94.664 | 164.462 | 1.00 | 34.49 |
| ATOM | 1957 | CA | LYS | 452 | 40.962 | 97.918 | 166.163 | 1.00 | 35.38 |
| ATOM | 1970 | CA | ALA | 453 | 41.503 | 96.317 | 169.572 | 1.00 | 28.00 |
| ATOM | 1976 | CA | PHE | 454 | 44.012 | 93.845 | 168.164 | 1.00 | 32.56 |
| ATOM | 1988 | CA | LEU | 455 | 46.236 | 96.653 | 166.861 | 1.00 | 40.19 |
| ATOM | 1997 | CA | LEU | 456 | 46.402 | 98.605 | 170.114 | 1.00 | 42.45 |
| ATOM | 2006 | CA | VAL | 457 | 46.966 | 95.358 | 172.060 | 1.00 | 38.09 |
| ATOM | 2014 | CA | GLN | 458 | 50.298 | 95.232 | 170.161 | 1.00 | 48.02 |
| ATOM | 2026 | CA | ASP | 459 | 51.630 | 98.529 | 171.587 | 1.00 | 41.96 |
| ATOM | 2035 | CA | ILE | 460 | 50.230 | 97.686 | 175.001 | 1.00 | 25.82 |
| ATOM | 2044 | CA | MET | 461 | 52.409 | 94.542 | 175.085 | 1.00 | 33.69 |
| ATOM | 2053 | CA | GLU | 462 | 55.702 | 96.253 | 173.969 | 1.00 | 45.36 |

APPENDIX 1-continued

| ATOM | 2063 | CA | ASP | 463 | 55.069 | 99.093 | 176.249 | 1.00 | 48.41 |
|---|---|---|---|---|---|---|---|---|---|
| ATOM | 2072 | CA | THR | 464 | 52.771 | 98.555 | 179.186 | 1.00 | 41.63 |
| ATOM | 2081 | CA | MET | 465 | 52.743 | 94.854 | 180.171 | 1.00 | 42.05 |
| ATOM | 2090 | CA | ARG | 466 | 56.333 | 94.928 | 181.338 | 1.00 | 44.99 |
| ATOM | 2107 | CA | PHE | 467 | 57.618 | 91.923 | 183.501 | 1.00 | 38.72 |
| ATOM | 2119 | CA | ARG | 468 | 61.258 | 90.894 | 184.513 | 1.00 | 50.64 |
| ATOM | 2136 | CA | ASP | 469 | 63.046 | 88.868 | 181.895 | 1.00 | 53.46 |
| ATOM | 2145 | CA | ASN | 470 | 62.896 | 85.096 | 181.832 | 1.00 | 52.84 |
| ATOM | 2156 | CA | THR | 471 | 60.211 | 84.798 | 184.479 | 1.00 | 47.58 |
| ATOM | 2165 | CA | PRO | 472 | 57.055 | 82.652 | 183.744 | 1.00 | 46.82 |
| ATOM | 2172 | CA | ASN | 473 | 54.971 | 85.777 | 183.172 | 1.00 | 38.75 |
| ATOM | 2183 | CA | ALA | 474 | 57.431 | 87.402 | 180.828 | 1.00 | 37.27 |
| ATOM | 2189 | CA | ILE | 475 | 57.795 | 84.219 | 178.807 | 1.00 | 32.85 |
| ATOM | 2198 | CA | ALA | 476 | 54.021 | 84.034 | 178.455 | 1.00 | 27.98 |
| ATOM | 2204 | CA | ILE | 477 | 53.844 | 87.522 | 176.756 | 1.00 | 30.47 |
| ATOM | 2213 | CA | VAL | 478 | 56.690 | 86.495 | 174.201 | 1.00 | 30.40 |
| ATOM | 2221 | CA | GLN | 479 | 54.381 | 83.711 | 173.325 | 1.00 | 31.18 |
| ATOM | 2233 | CA | LEU | 480 | 51.419 | 86.038 | 172.893 | 1.00 | 27.44 |
| ATOM | 2242 | CA | GLN | 481 | 53.392 | 88.551 | 170.821 | 1.00 | 31.59 |
| ATOM | 2254 | CA | GLU | 482 | 54.572 | 85.683 | 168.506 | 1.00 | 29.90 |
| ATOM | 2264 | CA | LEU | 483 | 50.900 | 84.532 | 168.340 | 1.00 | 22.16 |
| ATOM | 2273 | CA | SER | 484 | 50.077 | 88.156 | 167.451 | 1.00 | 29.37 |
| ATOM | 2281 | CA | LEU | 485 | 52.410 | 87.880 | 164.490 | 1.00 | 32.70 |
| ATOM | 2290 | CA | ARG | 486 | 50.865 | 84.572 | 163.229 | 1.00 | 30.59 |
| ATOM | 2307 | CA | LEU | 487 | 47.396 | 86.383 | 163.343 | 1.00 | 31.02 |
| ATOM | 2316 | CA | LYS | 488 | 48.292 | 89.399 | 161.352 | 1.00 | 34.90 |
| ATOM | 2329 | CA | SER | 489 | 47.728 | 87.397 | 158.200 | 1.00 | 35.68 |
| ATOM | 2337 | CA | CYS | 490 | 44.112 | 87.134 | 159.417 | 1.00 | 35.03 |
| ATOM | 2344 | CA | PHE | 491 | 43.520 | 90.786 | 159.602 | 1.00 | 42.73 |
| ATOM | 2356 | CA | THR | 492 | 43.145 | 93.174 | 156.663 | 1.00 | 56.24 |
| ATOM | 2365 | CA | ALA | 493 | 44.877 | 96.467 | 156.617 | 1.00 | 57.56 |
| ATOM | 2371 | CA | ASP | 494 | 42.318 | 99.142 | 157.302 | 1.00 | 57.16 |
| ATOM | 2380 | CA | ALA | 495 | 42.063 | 102.909 | 156.516 | 1.00 | 62.14 |
| ATOM | 2386 | CA | GLU | 496 | 45.542 | 104.198 | 157.805 | 1.00 | 64.30 |
| ATOM | 2396 | CA | GLU | 497 | 44.589 | 107.547 | 159.382 | 1.00 | 70.67 |
| ATOM | 2406 | CA | HIS | 498 | 41.577 | 105.660 | 160.752 | 1.00 | 75.16 |
| ATOM | 2419 | CA | ASP | 499 | 44.400 | 103.329 | 161.968 | 1.00 | 72.11 |
| ATOM | 2428 | CA | LYS | 500 | 44.773 | 105.712 | 164.874 | 1.00 | 65.63 |
| ATOM | 2441 | CA | ALA | 501 | 41.040 | 106.628 | 165.617 | 1.00 | 55.63 |
| ATOM | 2447 | CA | CYS | 502 | 38.563 | 105.427 | 168.336 | 1.00 | 53.33 |
| ATOM | 2454 | CA | VAL | 503 | 41.155 | 105.639 | 171.100 | 1.00 | 52.46 |
| ATOM | 2462 | CA | ARG | 504 | 39.866 | 106.944 | 174.425 | 1.00 | 51.00 |
| ATOM | 2479 | CA | THR | 505 | 42.588 | 106.921 | 177.117 | 1.00 | 50.42 |
| ATOM | 2488 | CA | PHE | 506 | 41.955 | 104.935 | 180.331 | 1.00 | 43.64 |
| ATOM | 2500 | CA | TYR | 507 | 43.306 | 105.190 | 183.809 | 1.00 | 41.84 |
| ATOM | 2514 | CA | GLU | 508 | 42.651 | 101.611 | 185.218 | 1.00 | 39.35 |
| ATOM | 2524 | CA | THR | 509 | 44.156 | 99.096 | 187.597 | 1.00 | 41.67 |
| ATOM | 2533 | CA | PRO | 510 | 46.618 | 96.563 | 185.969 | 1.00 | 39.70 |
| ATOM | 2540 | CA | LEU | 511 | 44.134 | 93.600 | 186.416 | 1.00 | 42.72 |
| ATOM | 2549 | CA | GLN | 512 | 41.460 | 95.632 | 184.624 | 1.00 | 37.47 |
| ATOM | 2561 | CA | LEU | 513 | 43.895 | 96.148 | 181.765 | 1.00 | 27.02 |
| ATOM | 2570 | CA | LEU | 514 | 44.769 | 92.421 | 181.627 | 1.00 | 24.55 |
| ATOM | 2579 | CA | GLU | 515 | 41.076 | 91.327 | 181.688 | 1.00 | 31.93 |
| ATOM | 2589 | CA | LYS | 516 | 40.903 | 93.442 | 178.515 | 1.00 | 31.96 |
| ATOM | 2602 | CA | VAL | 517 | 43.981 | 91.949 | 176.692 | 1.00 | 26.46 |
| ATOM | 2610 | CA | LYS | 518 | 42.528 | 88.538 | 177.852 | 1.00 | 30.83 |
| ATOM | 2623 | CA | ASN | 519 | 39.106 | 89.397 | 176.432 | 1.00 | 37.62 |
| ATOM | 2634 | CA | VAL | 520 | 40.221 | 90.488 | 172.933 | 1.00 | 35.75 |
| ATOM | 2642 | CA | PHE | 521 | 42.191 | 87.109 | 172.662 | 1.00 | 25.45 |
| ATOM | 2654 | CA | ASN | 522 | 39.292 | 85.079 | 173.953 | 1.00 | 26.73 |
| ATOM | 2665 | CA | GLU | 523 | 36.870 | 86.722 | 171.437 | 1.00 | 33.04 |
| ATOM | 2675 | CA | THR | 524 | 39.260 | 86.923 | 168.369 | 1.00 | 29.70 |
| ATOM | 2684 | CA | LYS | 525 | 39.423 | 83.195 | 169.011 | 1.00 | 28.41 |
| ATOM | 2697 | CA | ASN | 526 | 35.624 | 82.663 | 169.124 | 1.00 | 34.46 |
| ATOM | 2708 | CA | LEU | 527 | 34.816 | 84.653 | 166.021 | 1.00 | 28.09 |
| ATOM | 2717 | CA | LEU | 528 | 37.617 | 82.902 | 164.068 | 1.00 | 25.62 |
| ATOM | 2726 | CA | ASP | 529 | 35.899 | 79.662 | 164.964 | 1.00 | 35.00 |
| ATOM | 2735 | CA | LYS | 530 | 32.659 | 81.068 | 163.537 | 1.00 | 37.54 |
| ATOM | 2748 | CA | ASP | 531 | 34.250 | 82.150 | 160.272 | 1.00 | 37.92 |
| ATOM | 2757 | CA | TRP | 532 | 38.053 | 82.453 | 159.573 | 1.00 | 40.02 |
| ATOM | 2773 | CA | ASN | 533 | 38.395 | 85.446 | 157.159 | 1.00 | 42.64 |
| ATOM | 2784 | CA | ILE | 534 | 35.840 | 87.437 | 159.393 | 1.00 | 39.27 |
| ATOM | 2793 | CA | PHE | 535 | 38.635 | 89.996 | 159.881 | 1.00 | 40.49 |
| ATOM | 2805 | CA | SER | 536 | 38.485 | 90.720 | 156.238 | 1.00 | 46.56 |
| ATOM | 2813 | CA | LYS | 537 | 35.844 | 93.371 | 157.102 | 1.00 | 45.61 |
| ATOM | 2826 | CA | ASN | 538 | 35.653 | 96.936 | 155.760 | 1.00 | 54.39 |
| ATOM | 2837 | CA | CYS | 539 | 35.786 | 98.626 | 159.004 | 1.00 | 50.55 |
| ATOM | 2844 | CA | ASN | 540 | 36.738 | 101.888 | 157.286 | 1.00 | 58.49 |
| ATOM | 2855 | CA | ALA | 541 | 33.143 | 102.934 | 157.648 | 1.00 | 61.90 |

APPENDIX 1-continued

| ATOM | 2861 | CA | SER | 542 | 32.854 | 101.855 | 161.326 | 1.00 | 56.62 |
|------|------|----|-----|-----|--------|---------|---------|------|-------|
| ATOM | 2869 | CA | PHE | 543 | 35.911 | 103.888 | 162.235 | 1.00 | 55.25 |
| ATOM | 2881 | CA | ALA | 544 | 33.885 | 107.102 | 161.741 | 1.00 | 61.94 |
| ATOM | 2887 | CA | GLU | 545 | 30.949 | 107.003 | 164.203 | 1.00 | 63.83 |
| ATOM | 2897 | CA | CYS | 546 | 33.917 | 107.418 | 166.572 | 1.00 | 61.90 |
| ATOM | 2904 | CA | SER | 547 | 33.751 | 110.878 | 168.150 | 1.00 | 66.22 |
| ATOM | 2912 | CA | ALA | 548 | 37.461 | 110.300 | 168.811 | 1.00 | 65.91 |
| END  |      |    |     |     |        |         |         |      |       |

What is claimed is:

1. An isolated, purified, and soluble extracellular domain fragment of a human macrophage colony stimulating factor (M-CSF) receptor comprising the amino acid sequence of SEQ ID NO:11 and wherein said extracellular domain fragment does not comprise a transmembrane region.

2. An isolated, purified, and soluble extracellular domain fragment of a human macrophage colony stimulating factor (M-CSF) receptor consisting essentially of the amino acid sequence of SEQ ID NO:11 and wherein said extracellular domain fragment does not comprise a transmembrane region.

3. An isolated, purified, and soluble and dimerizing extracellular domain fragment of a human macrophage colony stimulating factor (M-CSF) receptor, wherein said extracellular domain fragment consists of the amino acid sequence of SEQ ID NO:11.

* * * * *